(12) United States Patent
Brosseau et al.

(10) Patent No.: US 8,841,325 B2
(45) Date of Patent: Sep. 23, 2014

(54) IMMUNOMODULATORY COMPOUNDS FOR THE RESTORATION OF VITAMIN D SENSITIVITY IN VITAMIN D RESISTANT TUMOR CELLS

(75) Inventors: Carole Brosseau, Cholet (FR); Justin Blake Bartlett, Basking Ridge, NJ (US); Angus George Dalgleish, Cheam (GB); Kay Winifred Colston, Thames Ditton (GB); Christine Galustian, Croydon (GB)

(73) Assignee: Celgene Corporation, Summit, NJ (US)

( * ) Notice: Subject to any disclaimer, the term of this patent is extended or adjusted under 35 U.S.C. 154(b) by 138 days.

(21) Appl. No.: 13/511,002

(22) PCT Filed: Nov. 24, 2010

(86) PCT No.: PCT/US2010/057951
§ 371 (c)(1),
(2), (4) Date: Dec. 11, 2012

(87) PCT Pub. No.: WO2011/066351
PCT Pub. Date: Jun. 3, 2011

(65) Prior Publication Data
US 2013/0171196 A1 Jul. 4, 2013

Related U.S. Application Data

(60) Provisional application No. 61/264,062, filed on Nov. 24, 2009, provisional application No. 61/324,473, filed on Apr. 15, 2010.

(51) Int. Cl.
*A61K 31/45* (2006.01)
*C07D 401/04* (2006.01)

(52) U.S. Cl.
USPC ........... 514/323; 546/184; 546/192; 546/200; 514/315; 514/319

(58) Field of Classification Search
CPC .............................. A61K 31/45; C07D 401/04
USPC ........... 546/184, 195, 200; 514/315, 319, 323
See application file for complete search history.

(56) References Cited

U.S. PATENT DOCUMENTS

2006/0172014 A1 8/2006 Curd et al.
2008/0286232 A1 11/2008 Zeldis
2012/0115804 A1 5/2012 Marik et al.

FOREIGN PATENT DOCUMENTS

WO WO 2006/036892 * 4/2006

OTHER PUBLICATIONS

Saini et al (2013): Expert Opin. Investig. Drugs, 22 (2), 207-215.*
Peterlik et al., Calcium, Vitamin D and Cancer, Anticancer Research, 2009, vol. 29, pp. 3687-3698.
Chen et. al., Meta-analysis of vitamin D, calcium and the prevention of breast cancer, Breast Cancer Res Treat., Jun. 2010, vol. 121, issue 2, pp. 469-477.
Abbas et al., Cancer Epidemiology, Biomarkers & Prevention, The Gc2 Allele of the Vitamin D Binding Protein is Associated with a Decreased Postmenopausal Breast Cancer Risk, Independent of the Vitamin D Status, 2008, vol. 17, pp. 1339-1343.
Kulie et al., Vitamin D: An Evidence-Based Review, Journal of American Board of Family Medicine, 2009, vol. 22, No. 6, pp. 698-706.
Kasukabe, et al., Control of Proliferating Potential of Myeloid Leukemia Cells During Long-Term Treatment with Vitamin D3 Analogues and Other Differentiation Inducers in Combination with Antileukemic Drugs: In Vitro and in Vivo Studies, Cancer Research, 1987, vol. 47, pp. 567-572.
International Search Report, PCT/US2010/057951, Feb. 8, 2011 (2 pages).
PCT Written Opinion, PCT/US2010/057951, Feb. 8, 2011 (5 pages).

* cited by examiner

*Primary Examiner* — Golam M M Shameem
(74) *Attorney, Agent, or Firm* — Dorf & Nelson LLP; Scott D. Locke, Esq.

(57) ABSTRACT

Provided herein are methods of restoring vitamin D sensitivity in tumor cells that are vitamin D resistant. Also provided are methods of treating, preventing or managing cancer using an immunomodulatory compound in combination with a vitamin D agent. Pharmaceutical compositions and single unit dosage forms suitable for use in the methods provided herein are also disclosed.

15 Claims, 19 Drawing Sheets

Cpd A: 1-oxo-2-(2,6-dioxopiperidin-3-yl)-4-aminoisoindoline
Cpd B: 1,3-dioxo-2-(2,6-dioxopiperidin-3-yl)-4-aminoisoindoline

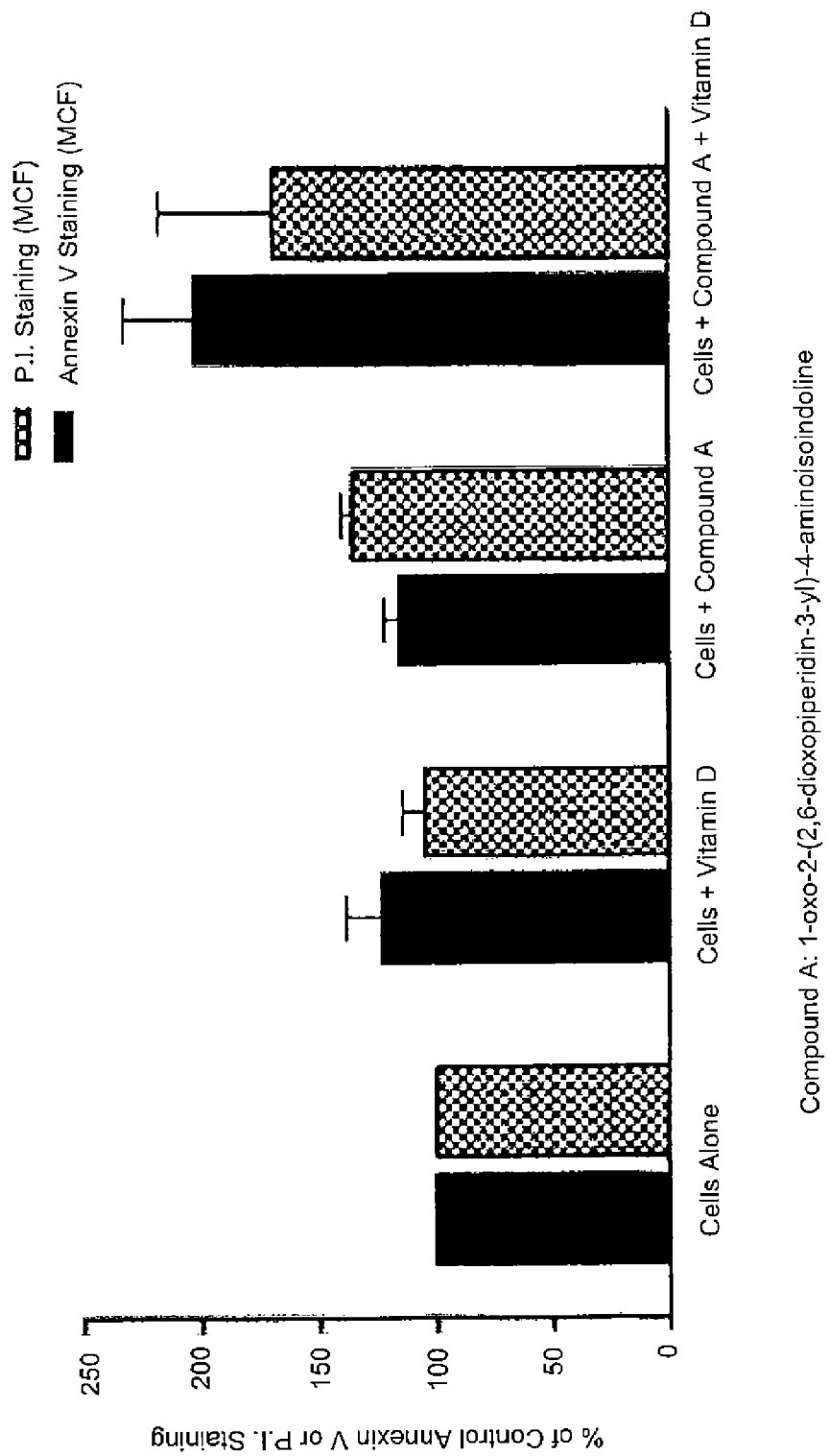

1 = Control
2 = 1, 25-$D_3$
3 = Lenalidomide
4 = 1, 25-$D_3$ + Lenalidomide

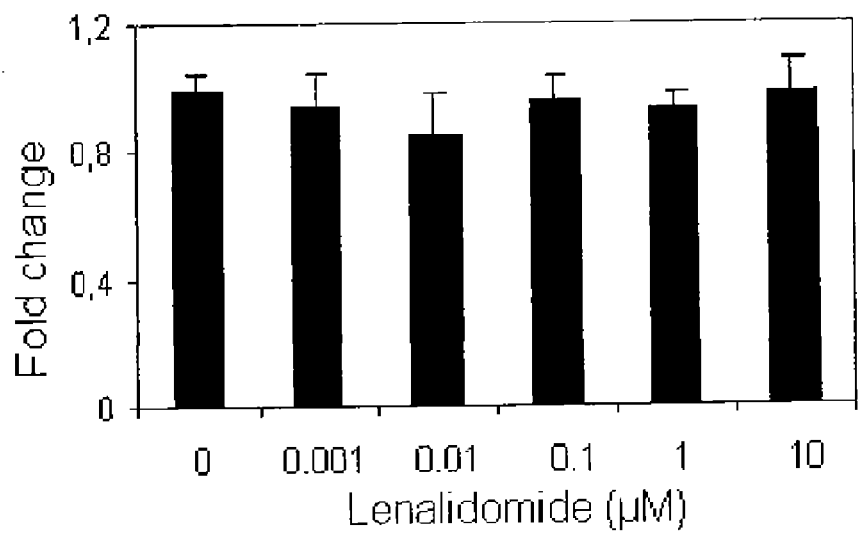
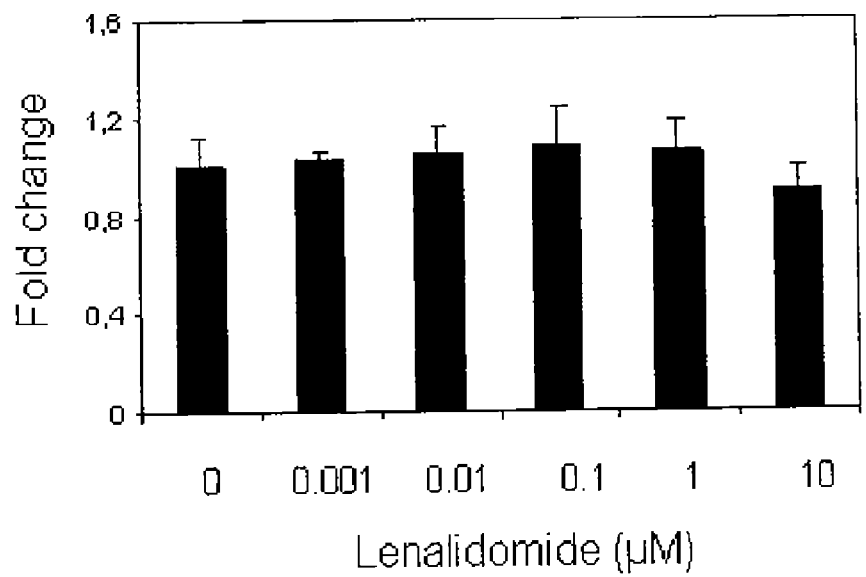
FIG. 13

IMMUNOMODULATORY COMPOUNDS FOR THE RESTORATION OF VITAMIN D SENSITIVITY IN VITAMIN D RESISTANT TUMOR CELLS

CROSS-REFERENCE TO RELATED APPLICATIONS

This application is a national stage application of PCT/US2010/057951, filed Nov. 24, 2010, which claims the benefit of the filing date of Provisional Application No. 61/324,473, filed Apr. 15, 2010, and Provisional Application No. 61/264,062 filed Nov. 24, 2009, both entitled "Immunomodulatory compounds for the restoration of vitamin D sensitivity in vitamin D resistant tumor cells." These entire disclosures are hereby incorporated by reference into the present disclosure.

FIELD

Provided herein are methods of restoring vitamin D sensitivity in vitamin D resistant tumor cells. Methods of treating cancer, pharmaceutical compositions and dosing regimens using the immunomodulatory compounds, in combination with vitamin D agents, are also provided.

BACKGROUND

Pathology of Cancer

Cancer is characterized primarily by an increase in the number of abnormal cells derived from a given normal tissue, invasion of adjacent tissues by these abnormal cells, or lymphatic or blood-borne spread of malignant cells to regional lymph nodes and to distant sites (metastasis). Clinical data and molecular biologic studies indicate that cancer is a multistep process that begins with minor preneoplastic changes, which may under certain conditions progress to neoplasia. The neoplastic lesion may evolve clonally and develop an increasing capacity for invasion, growth, metastasis, and heterogeneity, especially under conditions in which the neoplastic cells escape the host's immune surveillance. Roitt, I., Brostoff, J and Kale, D., *Immunology*, 17.1-17.12 (3rd ed., Mosby, St. Louis, Mo., 1993).

There is an enormous variety of cancers which are described in detail in the medical literature. Examples include cancer of the lung, colon, rectum, prostate, breast, brain, and intestine. The incidence of cancer continues to climb as the general population ages, as new cancers develop, and as susceptible populations (e.g., people infected with AIDS or excessively exposed to sunlight) grow. However, options for the treatment of cancer are limited. For example, in the case of blood cancers (e.g., multiple myeloma), few treatment options are available, especially when conventional chemotherapy fails and bone-marrow transplantation is not an option. A tremendous demand therefore exists for new methods and compositions that can be used to treat patients with cancer.

Many types of cancers are associated with new blood vessel formation, a process known as angiogenesis. Several of the mechanisms involved in tumor-induced angiogenesis have been elucidated. The most direct of these mechanisms is the secretion by the tumor cells of cytokines with angiogenic properties. Examples of these cytokines include acidic and basic fibroblast growth factor (a,b-FGF), angiogenin, vascular endothelial growth factor (VEGF), and TNF-γ. Alternatively, tumor cells can release angiogenic peptides through the production of proteases and the subsequent breakdown of the extracellular matrix where some cytokines are stored (e.g., b-FGF). Angiogenesis can also be induced indirectly through the recruitment of inflammatory cells (particularly macrophages) and their subsequent release of angiogenic cytokines (e.g., TNF-α, b-FGF).

Vitamin D Agents and Cancer

In addition to their primary role in maintaining bone mineralization, vitamin D agents have been shown to be effective as inhibitors of tumor cell growth. For example, in breast cancer cell lines, inhibitory effects on cell cycle arrest, angiogenesis, invasion and metastasis have been observed in addition to pro-apoptotic effects. In addition, vitamin D agents have been shown to inhibit and prevent breast cancer growth in several mouse models, and a correlation between vitamin D receptor expression on breast cancer cells and disease free survival of breast cancer patients has also been observed.

Despite the beneficial effects of vitamin D agents, limitations such as development of vitamin D resistance by tumor cells and hypercalcaemia present challenges in using vitamin D agents in cancer therapy. Thus, restoration of vitamin D sensitivity in tumor cells that develop vitamin D resistance would be a valuable therapeutic tool in cancer treatment.

Immunomodulatory Compounds

A number of studies have been conducted with the aim of providing compounds that can safely and effectively be used to treat diseases associated with abnormal production of TNF-α. See, e.g., Marriott, J. B., et al., *Expert Opin. Biol. Ther.* 1(4):1-8 (2001); G. W. Muller, et al., Journal of Medicinal Chemistry 39(17): 3238-3240 (1996); and G. W. Muller, et al., Bioorganic & Medicinal Chemistry Letters 8: 2669-2674 (1998). Some studies have focused on a group of compounds selected for their capacity to potently inhibit TNF-α production by LPS stimulated PBMC. L. G. Corral, et al., Ann Rheum. Dis. 58:(Suppl I) 1107-1113 (1999). These compounds, which are referred to as IMiDs™ (Celgene Corporation) or Immunomodulatory Drugs, show not only potent inhibition of TNF-α but also marked inhibition of LPS induced monocyte IL1β and IL12 production. LPS induced IL6 is also inhibited by immunomodulatory compounds, albeit partially. These compounds are potent stimulators of LPS induced IL10. Id. Particular examples of immunomodulatory compounds include, but are not limited to, the substituted 2-(2,6-dioxopiperidin-3-yl) phthalimides and substituted 2-(2,6-dioxopiperidin-3-yl)-1-oxoisoindoles described in U.S. Pat. Nos. 6,281,230 and 6,316,471, both to G. W. Muller, et al.

SUMMARY

Provided herein are methods of restoring vitamin D sensitivity in vitamin D resistant tumor cells. The methods comprise contacting an effective amount of an immunomodulatory compound, or a pharmaceutically acceptable salt, solvate (e.g., hydrate), stereoisomer, or prodrug thereof, with vitamin D resistant tumor cell.

Also provided herein are methods of treating cancer refractory to vitamin D treatment comprising administering an effective amount of an immunomodulatory compound provided herein, or a pharmaceutically acceptable salt, solvate, stereoisomer, or prodrug thereof, in combination with a vitamin D agent.

In some embodiments, one or more therapies conventionally used to treat, prevent or manage cancer may be additionally used. Examples of such conventional therapies include, but are not limited to, chemical agents and adaptive immunotherapy.

Also provided herein are pharmaceutical compositions, single unit dosage forms, dosing regimens and kits which comprise an immunomodulatory compound, or a pharmaceutically acceptable salt, solvate, stereoisomer, or prodrug thereof, and a vitamin D agent.

BRIEF DESCRIPTION OF FIGURES

FIG. 5 illustrates the results of Annexin V/PI staining tests performed on cells treated with 1,25 D3 alone, 1-oxo-2-(2,6-dioxopiperidin-3-yl)-4-aminoisoindoline alone, or 1,25 D3 and 1-oxo-2-(2,6-dioxopiperidin-3-3-yl)-4-aminoisoindoline in combination.

FIG. 13 illustrates the effects of lenalidomide treatment on MCF-7/VDR and HBL-100 viability.

DETAILED DESCRIPTION

Definitions

Figure 1:
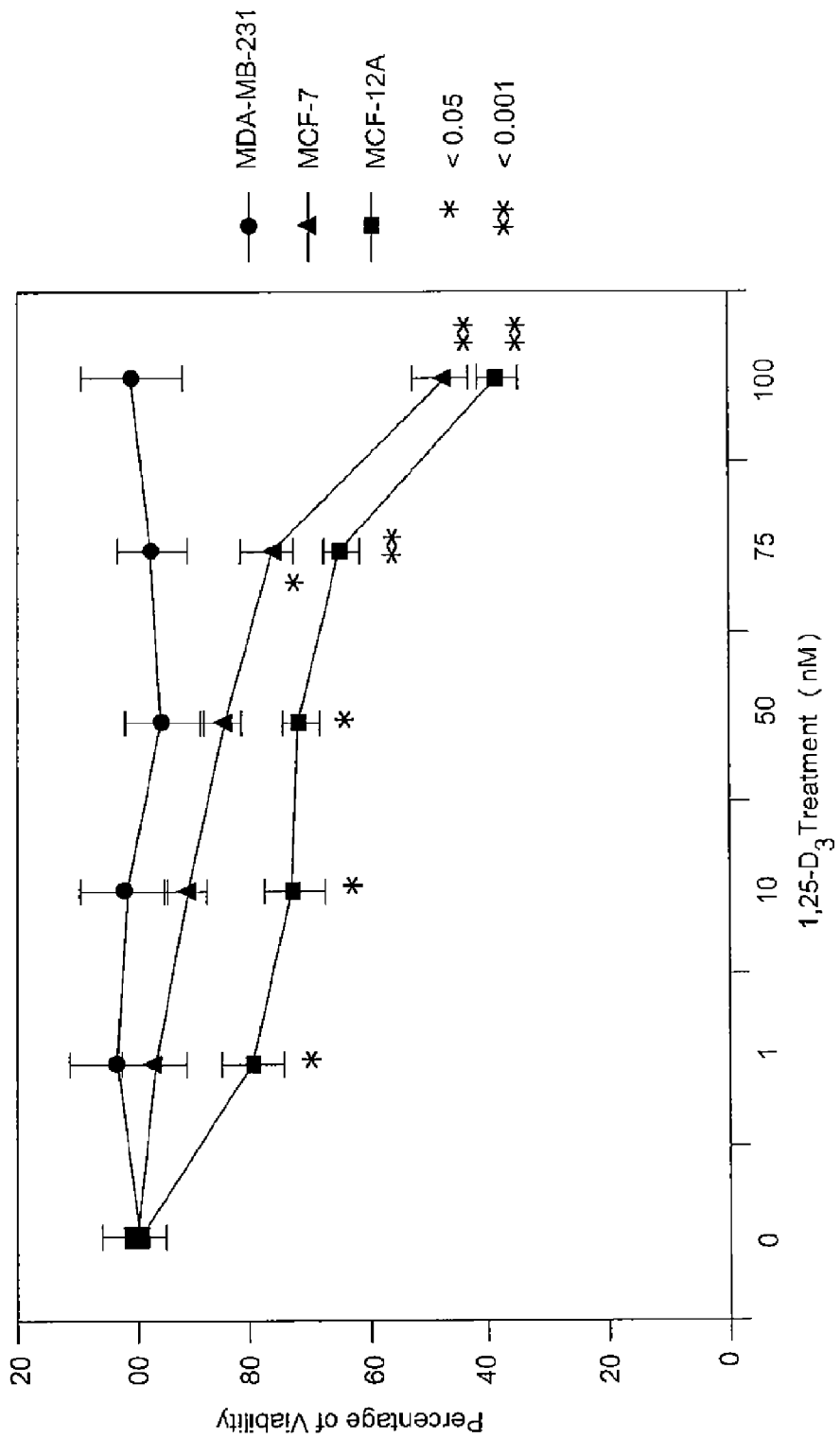
FIG. 1 illustrates effects of vitamin D on viability of MCF breast cancer cell variants MCF-12A, MDF7 and MDA-MB-231.

As used herein and unless otherwise indicated, the term "pharmaceutically acceptable salt" encompasses non-toxic acid and base addition salts of the compound to which the term refers. Acceptable non-toxic acid addition salts include those derived from organic and inorganic acids or bases known in the art, which include, for example, hydrochloric acid, hydrobromic acid, phosphoric acid, sulfuric acid, methanesulphonic acid, acetic acid, tartaric acid, lactic acid, succinic acid, citric acid, malic acid, maleic acid, sorbic acid, aconitic acid, salicylic acid, phthalic acid, embolic acid, enanthic acid, and the like.

Compounds that are acidic in nature are capable of forming salts with various pharmaceutically acceptable bases. The bases that can be used to prepare pharmaceutically acceptable base addition salts of such acidic compounds are those that form non-toxic base addition salts, i.e., salts containing pharmacologically acceptable cations such as, but not limited to, alkali metal or alkaline earth metal salts and the calcium, magnesium, sodium or potassium salts in particular. Suitable organic bases include, but are not limited to, N,N-dibenzylethylenediamine, chloroprocaine, choline, diethanolamine, ethylenediamine, meglumaine (N-methylglucamine), lysine, and procaine.

As used herein and unless otherwise indicated, the term "prodrug" means a derivative of a compound that can hydrolyze, oxidize, or otherwise react under biological conditions (in vitro or in vivo) to provide the compound. Examples of prodrugs include, but are not limited to, derivatives of immunomodulatory compounds that comprise biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Other examples of prodrugs include derivatives of immunomodulatory compounds that comprise —NO, —NO$_2$, —ONO, or —ONO$_2$ moieties. Prodrugs can typically be prepared using well-known methods, such as those described in 1 *Burger's Medicinal Chemistry and Drug Discovery*, 172-178, 949-982 (Manfred E. Wolff ed., 5th ed. 1995), and *Design of Prodrugs* (H. Bundgaard ed., Elsevier, New York 1985).

As used herein and unless otherwise indicated, the terms "biohydrolyzable amide," "biohydrolyzable ester," "biohydrolyzable carbamate," "biohydrolyzable carbonate," "biohydrolyzable ureide," "biohydrolyzable phosphate" mean an amide, ester, carbamate, carbonate, ureide, or phosphate, respectively, of a compound that either: 1) does not interfere with the biological activity of the compound but can confer upon that compound advantageous properties in vivo, such as uptake, duration of action, or onset of action; or 2) is biologically inactive but is converted in vivo to the biologically active compound. Examples of biohydrolyzable esters include, but are not limited to, lower alkyl esters, lower acyloxyalkyl esters (such as acetoxylmethyl, acetoxyethyl, aminocarbonyloxymethyl, pivaloyloxymethyl, and pivaloyloxyethyl esters), lactonyl esters (such as phthalidyl and thiophthalidyl esters), lower alkoxyacyloxyalkyl esters (such as methoxycarbonyl-oxymethyl, ethoxycarbonyloxyethyl and isopropoxycarbonyloxyethyl esters), alkoxyalkyl esters, choline esters, and acylamino alkyl esters (such as acetamidomethyl esters). Examples of biohydrolyzable amides include, but are not limited to, lower alkyl amides, α-amino acid amides, alkoxyacyl amides, and alkylaminoalkylcarbonyl amides. Examples of biohydrolyzable carbamates include, but are not limited to, lower alkylamines, substituted ethylenediamines, amino acids, hydroxyalkylamines, heterocyclic and heteroaromatic amines, and polyether amines.

The immunomodulatory compound for use in the methods and compositions contains a chiral center, and thus can exist as a racemic mixture of R and S enantiomers. The methods and compositions provided herein encompass the use of stereomerically pure forms of this compound, as well as the use of mixtures of those forms. For example, mixtures comprising equal or unequal amounts of the enantiomers may be used in methods and compositions provided herein. These isomers may be asymmetrically synthesized or resolved using standard techniques such as chiral columns or chiral resolving agents. See, e.g., Jacques, J., et al., *Enantiomers, Racemates and Resolutions* (Wiley-Interscience, New York, 1981); Wilen, S. H., et al., *Tetrahedron* 33:2725 (1977); Eliel, E. L., *Stereochemistry of Carbon Compounds* (McGraw-Hill, NY, 1962); and Wilen, S. H., *Tables of Resolving Agents and Optical Resolutions* p. 268 (E. L. Eliel, Ed., Univ. of Notre Dame Press, Notre Dame, Ind., 1972).

As used herein and unless otherwise indicated, the term "stereomerically pure" means that a compound substantially comprises one stereoisomer, and is substantially free of other stereoisomers. For example, a stereomerically pure compound having one chiral center will substantially comprise one enantiomer and will be substantially free of the opposite enantiomer. A stereomerically pure compound having two chiral centers will substantially comprise one stereoisomer (e.g., diastereoisomer) and will be substantially free of other diastereomers of the compound. A typical stereomerically pure compound comprises greater than about 80% by weight of one stereoisomer of the compound and less than about 20% by weight of other stereoisomers of the compound, greater than about 90% by weight of one stereoisomer of the compound and less than about 10% by weight of the other stereoisomers of the compound, greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound. As used herein and unless otherwise indicated, the term "stereomerically enriched" means a composition that comprises greater than about 60% by weight of one stereoisomer of a compound, greater than about 70% by weight, or greater than about 80% by weight of one stereoisomer of a compound. As used herein and unless otherwise indicated, the term "enantiomerically pure" means a stereomerically pure composition of a compound having one chiral center. Similarly, the term "stereomerically enriched" means a stereomerically enriched composition of a compound having one chiral center. In other words, the methods provided herein encompass the use of the R or S enantiomer of the immunomodulatory compound.

As used herein, unless otherwise specified, the term "treating" refers to the administration of a compound provided herein, with or without other additional active agent, after the onset of symptoms of the particular disease.

As used herein, unless otherwise specified, the term "preventing" refers to the treatment with or administration of an immunomodulatory compound, with or without other additional active compound, prior to the onset of symptoms, particularly to patients at risk of transverse myelitis and/or other disorders. The term "prevention" includes the inhibition or reduction of a symptom of the particular disease. Patients with familial history of a disease in particular are candidates for preventive regimens in certain embodiments. In addition, patients who have a history of recurring symptoms are also potential candidates for the prevention. In this regard, the term "prevention" may be interchangeably used with the term "prophylactic treatment."

As used herein and unless otherwise indicated, the term "managing" encompasses treating a patient who had suffered from the particular disease in an attempt to prevent or minimize the recurrence of the disease and/or reducing mortality rates of the patients.

As used herein and unless otherwise indicated, the term "vitamin D agent" encompasses vitamin D in its various forms (e.g., 1α,25-dihydrovitamin D3 ("1,25 D3"), a metabolite of vitamin D (e.g., 1α,25-dihydroxycholecalciferol)), or a derivative of vitamin D, an analog of vitamin D, and a pharmaceutically acceptable salt thereof.

Methods of Treatment, Prevention and Management

Provided herein are methods of restoring vitamin D sensitivity in vitamin D resistant tumor cells. The methods comprise contacting an effective amount of an immunomodulatory compound, or a pharmaceutically acceptable salt, solvate (e.g., hydrate), stereoisomer, or prodrug thereof, with vitamin D resistant tumor cell.

Also provided herein are methods of treating cancer refractory to vitamin D treatment comprising administering an effective amount of an immunomodulatory compound provided herein, or a pharmaceutically acceptable salt, solvate, stereoisomer, or prodrug thereof, in combination with a vitamin D agent.

Without being limited by a particular theory, the combination of an immunomodulatory compound and a vitamin D agent result in synergistic effects in treating cancer particularly cancer refractory to vitamin D treatment. Without being limited by a particular theory, it is believed that the inefficiency of vitamin D therapy is due, at least in part, to vitamin D resistance developed by tumor cells, and the synergistic effect observed by the combination for the treatment of vitamin D resistant tumor cells is in part a result of restoration of vitamin D sensitivity by an immunomodulatory compound.

Immunomodulatory Compounds

As used herein and unless otherwise indicated, the terms "immunomodulatory compounds" encompass certain small organic molecules that inhibit LPS induced monocyte TNF-α, IL-1β, IL-12, IL-6, MIP-1α, MCP-1, GM-CSF, G-CSF, and COX-2 production. Specific immunomodulatory compounds are discussed below.

TNF-α is an inflammatory cytokine produced by macrophages and monocytes during acute inflammation. TNF-α is responsible for a diverse range of signaling events within cells. Without being limited by a particular theory, one of the biological effects exerted by the immunomodulatory compounds provided herein is the reduction of myeloid cell TNF-α production Immunomodulatory compounds of provided herein may enhance the degradation of TNF-α mRNA.

Specific examples of immunomodulatory compounds include cyano and carboxy derivatives of substituted styrenes such as those disclosed in U.S. Pat. No. 5,929,117; 1-oxo-2-(2,6-dioxo-3-fluoropiperidin-3-yl) isoindolines and 1,3-dioxo-2-(2,6-dioxo-3-fluoropiperidine-3-yl) isoindolines such as those described in U.S. Pat. Nos. 5,874,448 and 5,955,476; the tetra substituted 2-(2,6-dioxopiperidin-3-yl)-1-oxoisoindolines described in U.S. Pat. No. 5,798,368; 1-oxo and 1,3-dioxo-2-(2,6-dioxopiperidin-3-yl) isoindolines (e.g., 4-methyl derivatives of thalidomide), substituted 2-(2,6- dioxopiperidin-3-yl) phthalimides and substituted 2-(2,6-dioxopiperidin-3-yl)-1-oxoisoindoles including, but not limited to, those disclosed in U.S. Pat. Nos. 5,635,517, 6,281,230, 6,316,471, 6,403,613, 6,476,052 and 6,555,554; 1-oxo and 1,3-dioxoisoindolines substituted in the 4-or 5-position of the indoline ring (e.g., 4-(4-amino-1,3-dioxoisoindoline-2-yl)-4-carbamoylbutanoic acid) described in U.S. Pat. No. 6,380,239; isoindoline-1-one and isoindoline-1,3-dione substituted in the 2-position with 2,6-dioxo-3-hydroxypiperidin-5-yl (e.g., 2-(2,6-dioxo-3-hydroxy-5-fluoropiperidin-5-yl)-4-aminoisoindolin-1-one) described in U.S. Pat. No. 6,458,810; a class of non-polypeptide cyclic amides disclosed in U.S. Pat. Nos. 5,698,579 and 5,877,200; and isoindole-imide compounds such as those described in U.S. patent publication no. 2003/0045552 published on Mar. 6, 2003, U.S. patent publication no. 2003/0096841 published on May 22, 2003, and International Application No. PCT/US01/50401 (International Publication No. WO 02/059106). The entireties of each of the patents and patent applications identified herein are incorporated herein by reference. Immunomodulatory compounds do not include thalidomide.

Various immunomodulatory compounds provided herein contain one or more chiral centers, and can exist as racemic mixtures of enantiomers or mixtures of diastereomers. The methods and compositions herein encompass the use of stereomerically pure forms of such compounds, as well as the use of mixtures of those forms. For example, mixtures comprising equal or unequal amounts of the enantiomers of a particular immunomodulatory compounds may be used in methods and compositions provided herein. These isomers may be asymmetrically synthesized or resolved using standard techniques such as chiral columns or chiral resolving agents. See, e.g., Jacques, J., et al., *Enantiomers, Racemates and Resolutions* (Wiley-Interscience, New York, 1981); Wilen, S. H., et al., *Tetrahedron* 33:2725 (1977); Eliel, E. L., *Stereochemistry of Carbon Compounds* (McGraw-Hill, NY, 1962); and Wilen, S. H., *Tables of Resolving Agents and Optical Resolutions* p. 268 (E. L. Eliel, Ed., Univ. of Notre Dame Press, Notre Dame, Ind., 1972).

In one embodiment, immunomodulatory compounds provided include, but are not limited to, 1-oxo-and 1,3 dioxo-2-(2,6-dioxopiperidin-3-yl) isoindolines substituted with amino in the benzo ring as described in U.S. Pat. No. 5,635,517 which is incorporated herein by reference. These compounds have the structure I:

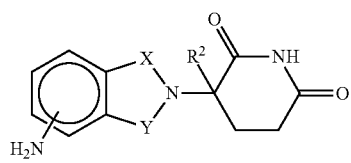

in which one of X and Y is C=O, the other of X and Y is C=O or $CH_2$, and $R^2$ is hydrogen or lower alkyl, in particular methyl. Specific immunomodulatory compounds include, but are not limited to:

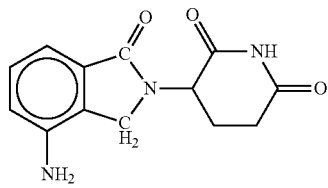

1-oxo-2-(2,6-dioxopiperidin-3-yl)-4-aminoisoindoline;

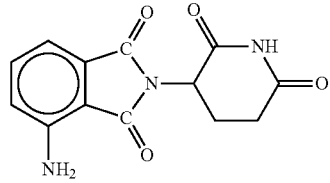

1,3-dioxo-2-(2,6-dioxopiperidin-3-yl)-4-aminoisoindoline; and

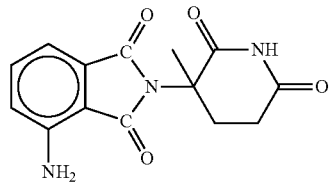

1,3-dioxo-2-(3-methyl-2,6-dioxopiperidin-3-yl)-4-aminoisoindole, and optically pure isomers thereof. The compounds can be obtained via standard, synthetic methods (see e.g., U.S. Pat. No. 5,635,517, incorporated herein by reference). The compounds are also available from Celgene Corporation, Warren, N.J.

As used herein, and unless otherwise indicated, the term "optically pure" means a composition that comprises one optical isomer of a compound and is substantially free of other isomers of that compound. For example, an optically pure composition of a compound having one chiral center will be substantially free of the opposite enantiomer of the compound. An optically pure composition of a compound having two chiral centers will be substantially free of other diastereomers of the compound. A typical optically pure compound comprises greater than about 80% by weight of one enantiomer of the compound and less than about 20% by weight of other enantiomers of the compound, greater than about 90% by weight of one enantiomer of the compound and less than about 10% by weight of the other enantiomers of the compound, greater than about 95% by weight of one enantiomer of the compound and less than about 5% by weight of the other enantiomers of the compound, greater than about 97% by weight of one enantiomer of the compound and less than about 3% by weight of the other enantiomers of the compound or greater than about 99% by weight of one enantiomer of the compound and less than about 1% by weight of the other enantiomers of the compound.

Other specific immunomodulatory compounds belong to a class of substituted 2-(2,6-dioxopiperidin-3-yl) phthalimides and substituted 2-(2,6-dioxopiperidin-3-yl)-1-oxoisoindoles, such as those described in U.S. Pat. Nos. 6,281,230; 6,316,471; 6,335,349; and 6,476,052, and International Patent Application No. PCT/US97/13375 (International Publication No. WO 98/03502), each of which is incorporated herein by reference. Representative compounds are of formula:

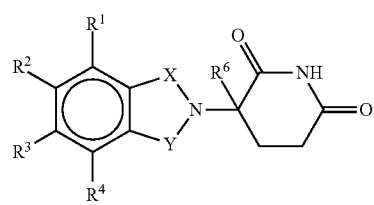

in which:
one of X and Y is C=O and the other of X and Y is C=O or CH$_2$;
(i) each of R$^1$, R$^2$, R$^3$, and R$^4$, independently of the others, is halo, alkyl of 1 to 4 carbon atoms, or alkoxy of 1 to 4 carbon atoms or (ii) one of R$^1$, R$^2$, R$^3$, and R$^4$ is —NHR$^5$ and the remaining of R$^1$, R$^2$, R$^3$, and R$^4$ are hydrogen;
R$^5$ is hydrogen or alkyl of 1 to 8 carbon atoms;
R$^6$ is hydrogen, alkyl of 1 to 8 carbon atoms, benzyl, or halo;
provided that R$^6$ is other than hydrogen if X and Y are C=O and (i) each of R$^1$, R$^2$, R$^3$, and R$^4$ is fluoro or (ii) one of R$^1$, R$^2$, R$^3$, or R$^4$ is amino.
Compounds representative of this class are of the formulas:

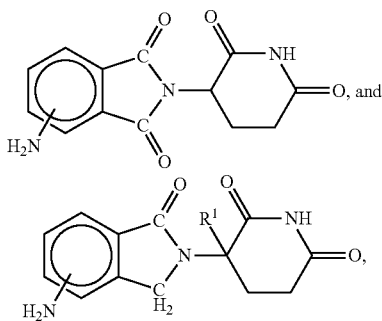

wherein R$^1$ is hydrogen or methyl. In a separate embodiment, the methods and compositions provided herein encompass the use of enantiomerically pure forms (e.g. optically pure (R) or (S) enantiomers) of these compounds.

Still other specific immunomodulatory compounds belong to a class of isoindole-imides disclosed in U.S. Patent Application Publication Nos. US 2003/0096841 and US 2003/0045552, and International Application No. PCT/US01/50401 (International Publication No. WO 02/059106), each of which are incorporated herein by reference. Representative compounds are of formula II:

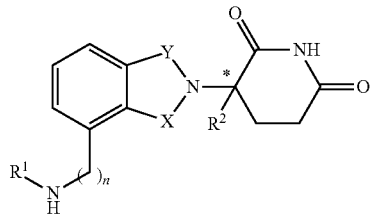

and pharmaceutically acceptable salts, hydrates, solvates, clathrates, enantiomers, diastereomers, racemates, and mixtures of stereoisomers thereof, wherein:
one of X and Y is C=O and the other is CH$_2$ or C=O;
R$^1$ is H, (C$_1$-C$_8$)alkyl, (C$_3$-C$_7$)cycloalkyl, (C$_2$-C$_8$)alkenyl, (C$_2$-C$_8$)alkynyl, benzyl, aryl, (C$_0$-C$_4$)alkyl-(C$_1$-C$_6$)heterocycloalkyl, (C$_0$-C$_4$)alkyl-(C$_2$-C$_5$)heteroaryl, C(O)R$^3$, C(S)R$^3$, C(O)OR$^4$, (C$_1$-C$_8$)alkyl-N(R$^6$)$_2$, (C$_1$-C$_8$)alkyl-OR$^5$, (C$_1$-C$_8$)alkyl-C(O)OR$^5$, C(O)NHR$^3$, C(S)NHR$^3$, C(O)NR$^3$R$^{3'}$, C(S)NR$^3$R$^{3'}$ or (C$_1$-C$_8$)alkyl-O(CO)R$^5$;
R$^2$ is H, F, benzyl, (C$_1$-C$_8$)alkyl, (C$_2$-C$_8$)alkenyl, or (C$_2$-C$_8$)alkynyl;
R$^3$ and R$^{3'}$ are independently (C$_1$-C$_8$)alkyl, (C$_3$-C$_7$)cycloalkyl, (C$_2$-C$_8$)alkenyl, (C$_2$-C$_8$)alkynyl, benzyl, aryl, (C$_0$-C$_4$)alkyl-(C$_1$-C$_6$)heterocycloalkyl, (C$_0$-C$_4$)alkyl-(C$_2$-C$_5$)heteroaryl, (C$_0$-C$_8$)alkyl-N(R$^6$)$_2$, (C$_1$-C$_8$)alkyl-OR$^5$, (C$_1$-C$_8$)alkyl-C(O)OR$^5$, (C$_1$-C$_8$)alkyl-O(CO)R$^5$, or C(O)OR$^5$;
R$^4$ is (C$_1$-C$_8$)alkyl, (C$_2$-C$_8$)alkenyl, (C$_2$-C$_8$)alkynyl, (C$_1$-C$_4$)alkyl-OR$^5$, benzyl, aryl, (C$_0$-C$_4$)alkyl-(C$_1$-C$_6$)heterocycloalkyl, or (C$_0$-C$_4$)alkyl-(C$_2$-C$_5$)heteroaryl;
R$^5$ is (C$_1$-C$_8$)alkyl, (C$_2$-C$_8$)alkenyl, (C$_2$-C$_8$)alkynyl, benzyl, aryl, or (C$_2$-C$_5$)heteroaryl;
each occurrence of R$^6$ is independently H, (C$_1$-C$_8$)alkyl, (C$_2$-C$_8$)alkenyl, (C$_2$-C$_8$)alkynyl, benzyl, aryl, (C$_2$-C$_5$)heteroaryl, or (C$_0$-C$_8$)alkyl-C(O)O—R$^5$ or the R$^6$ groups can join to form a heterocycloalkyl group;
n is 0 or 1; and
* represents a chiral-carbon center.

In specific compounds of formula II, when n is 0 then R$^1$ is (C$_3$-C$_7$)cycloalkyl, (C$_2$-C$_8$)alkenyl, (C$_2$-C$_8$)alkynyl, benzyl, aryl, (C$_0$-C$_4$)alkyl-(C$_1$-C$_6$)heterocycloalkyl, (C$_0$-C$_4$)alkyl-(C$_2$-C$_5$)heteroaryl, C(O)R$^3$, C(O)OR$^4$, (C$_1$-C$_8$)alkyl-N(R$^6$)$_2$, (C$_1$-C$_8$)alkyl-OR$^5$, (C$_1$-C$_8$)alkyl-C(O)OR$^5$, C(S)NHR$^3$, or (C$_1$-C$_8$)alkyl-O(CO)R$^5$;
R$^2$ is H or (C$_1$-C$_8$)alkyl; and
R$^3$ is (C$_1$-C$_8$)alkyl, (C$_3$-C$_7$)cycloalkyl, (C$_2$-C$_8$)alkenyl, (C$_2$-C$_8$)alkynyl, benzyl, aryl, (C$_0$-C$_4$)alkyl-(C$_1$-C$_6$)heterocycloalkyl, (C$_0$-C$_4$)alkyl-(C$_2$-C$_5$)heteroaryl, (C$_5$-C$_8$)alkyl-N(R$^6$)$_2$; (C$_0$-C$_8$)alkyl-NH—C(O)O—R$^5$; (C$_1$-C$_8$)alkyl-OR$^5$, (C$_1$-C$_8$)alkyl-C(O)OR$^5$, (C$_1$-C$_8$)alkyl-O(CO)R$^5$, or C(O)OR$^5$; and the other variables have the same definitions.

In other specific compounds of formula II, R$^2$ is H or (C$_1$-C$_4$)alkyl.

In other specific compounds of formula II, R$^1$ is (C$_1$-C$_8$)alkyl or benzyl.

In other specific compounds of formula II, R$^1$ is H, (C$_1$-C$_8$)alkyl, benzyl, CH$_2$OCH$_3$, CH$_2$CH$_2$OCH$_3$, or

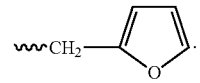

In another embodiment of the compounds of formula II, R$^1$ is

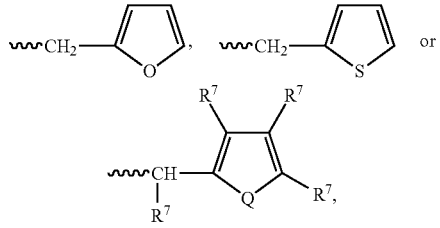

wherein Q is O or S, and each occurrence of R$^7$ is independently H, (C$_1$-C$_8$)alkyl, (C$_3$-C$_7$)cycloalkyl, (C$_2$-C$_8$)alkenyl, (C$_2$-C$_8$)alkynyl, benzyl, aryl, halogen, (C$_0$-C$_4$)alkyl-(C$_1$-C$_6$)heterocycloalkyl, (C$_0$-C$_4$)alkyl-(C$_2$-C$_5$)heteroaryl, (C$_0$-C$_8$)alkyl-N(R$^6$)$_2$, (C$_1$-C$_8$)alkyl-OR$^5$, (C$_1$-C$_8$)alkyl-C(O)OR$^5$, (C$_1$-C$_8$)alkyl-O(CO)R$^5$, or C(O)OR$^5$, or adjacent occurrences of R$^7$ can be taken together to form a bicyclic alkyl or aryl ring.

In other specific compounds of formula II, R$^1$ is C(O)R$^3$.

In other specific compounds of formula II, R$^3$ is (C$_0$-C$_4$)alkyl-(C$_2$-C$_5$)heteroaryl, (C$_1$-C$_8$)alkyl, aryl, or (C$_0$-C$_4$)alkyl-OR$^5$.

In other specific compounds of formula II, heteroaryl is pyridyl, furyl, or thienyl.

In other specific compounds of formula II, $R^1$ is $C(O)OR^4$.

In other specific compounds of formula II, the H of C(O)NHC(O) can be replaced with $(C_1-C_4)$alkyl, aryl, or benzyl.

Further examples of the compounds in this class include, but are not limited to: [2-(2,6-dioxo-piperidin-3-yl)-1,3-dioxo-2,3-dihydro-1H-isoindol-4-ylmethyl]-amide; (2-(2,6-dioxo-piperidin-3-yl)-1,3-dioxo-2,3-dihydro-1H-isoindol-4-ylmethyl)-carbamic acid tert-butyl ester; 4-(aminomethyl)-2-(2,6-dioxo(3-piperidyl))-isoindoline-1,3-dione; N-(2-(2,6-dioxo-piperidin-3-yl)-1,3-dioxo-2,3-dihydro-1H-isoindol-4-ylmethyl)-acetamide; N-{(2-(2,6-dioxo(3-piperidyl)-1,3-dioxoisoindolin-4-yl)methyl}cyclopropyl-carboxamide; 2-chloro-N-{(2-(2,6-dioxo(3-piperidyl))-1,3-dioxoisoindolin-4-yl)methyl}acetamide; N-(2-(2,6-dioxo(3-piperidyl))-1,3-dioxoisoindolin-4-yl)-3-pyridylcarboxamide; 3-{1-oxo-4-(benzylamino)isoindolin-2-yl}piperidine-2,6-dione; 2-(2,6-dioxo(3-piperidyl))-4-(benzylamino)isoindoline-1,3-dione; N-{(2-(2,6-dioxo(3-piperidyl))-1,3-dioxoisoindolin-4-yl)methyl}propanamide; N-{(2-(2,6-dioxo(3-piperidyl))-1,3-dioxoisoindolin-4-yl)methyl}-3-pyridylcarboxamide; N-{(2-(2,6-dioxo(3-piperidyl))-1,3-dioxoisoindolin-4-yl)methyl}heptanamide; N-{(2-(2,6-dioxo(3-piperidyl))-1,3-dioxoisoindolin-4-yl)methyl}-2-furylcarboxamide; {N-(2-(2,6-dioxo(3-piperidyl))-1,3-dioxoisoindolin-4-yl) carbamoyl}methyl acetate; N-(2-(2,6-dioxo(3-piperidyl))-1,3-dioxoisoindolin-4-yl)pentanamide; N-(2-(2,6-dioxo(3-piperidyl))-1,3-dioxoisoindolin-4-yl)-2-thienylcarboxamide; N-{[2-(2,6-dioxo(3-piperidyl))-1,3-dioxoisoindolin-4-yl]methyl}(butylamino)carboxamide; N-{[2-(2,6-dioxo(3-piperidyl))-1,3-dioxoisoindolin-4-yl]methyl}(octylamino)carboxamide; and N-{[2-(2,6-dioxo(3-piperidyl))-1,3-dioxoisoindolin-4-yl]methyl}(benzylamino)carboxamide.

Still other specific immunomodulatory compounds belong to a class of isoindole-imides disclosed in U.S. Patent Application Publication Nos. US 2002/0045643, International Publication No. WO 98/54170, and U.S. Pat. No. 6,395,754, each of which is incorporated herein by reference. Representative compounds are of formula III:

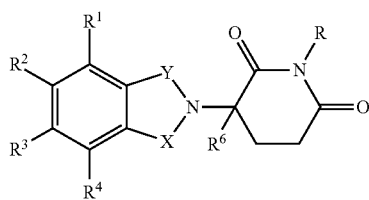

III and pharmaceutically acceptable salts, hydrates, solvates, clathrates, enantiomers, diastereomers, racemates, and mixtures of stereoisomers thereof, wherein:

one of X and Y is C=O and the other is $CH_2$ or C=O;

R is H or $CH_2OCOR'$;

(i) each of $R^1$, $R^2$, $R^3$, or $R^4$, independently of the others, is halo, alkyl of 1 to 4 carbon atoms, or alkoxy of 1 to 4 carbon atoms or (ii) one of $R^1$, $R^2$, $R^3$, or $R^4$ is nitro or $-NHR^5$ and the remaining of $R^1$, $R^2$, $R^3$, or $R^4$ are hydrogen;

$R^5$ is hydrogen or alkyl of 1 to 8 carbons $R^6$ hydrogen, alkyl of 1 to 8 carbon atoms, benzo, chloro, or fluoro;

R' is $R^7-CHR^{10}-N(R^8R^9)$;

$R^7$ is m-phenylene or p-phenylene or $-(C_nH_{2n})-$ in which n has a value of 0 to 4;

each of $R^8$ and $R^9$ taken independently of the other is hydrogen or alkyl of 1 to 8 carbon atoms, or $R^8$ and $R^9$ taken together are tetramethylene, pentamethylene, hexamethylene, or $-CH_2CH_2X_1CH_2CH_2-$ in which $X_1$ is $-O-$, $-S-$, or $-NH-$;

$R^{10}$ is hydrogen, alkyl of to 8 carbon atoms, or phenyl; and

* represents a chiral-carbon center.

Other representative compounds are of formula:

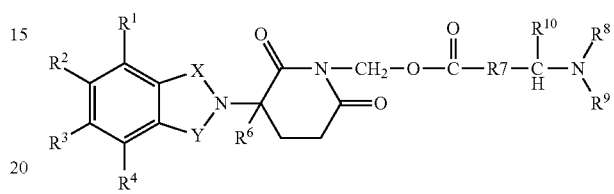

wherein:

one of X and Y is C=O and the other of X and Y is C=O or $CH_2$;

(i) each of $R^1$, $R^2$, $R^3$, or $R^4$, independently of the others, is halo, alkyl of 1 to 4 carbon atoms, or alkoxy of 1 to 4 carbon atoms or (ii) one of $R^1$, $R^2$, $R^3$, and $R^4$ is $-NHR^5$ and the remaining of $R^1$, $R^2$, $R^3$, and $R^4$ are hydrogen;

$R^5$ is hydrogen or alkyl of 1 to 8 carbon atoms;

$R^6$ is hydrogen, alkyl of 1 to 8 carbon atoms, benzo, chloro, or fluoro;

$R^7$ is m-phenylene or p-phenylene or $-(C_nH_{2n})-$ in which n has a value of 0 to 4;

each of $R^8$ and $R^9$ taken independently of the other is hydrogen or alkyl of 1 to 8 carbon atoms, or $R^8$ and $R^9$ taken together are tetramethylene, pentamethylene, hexamethylene, or $-CH_2CH_2 X^1CH_2CH_2-$ in which $X^1$ is $-O-$, $-S-$, or $-NH-$; and $R^{10}$ is hydrogen, alkyl of to 8 carbon atoms, or phenyl.

Other representative compounds are of formula:

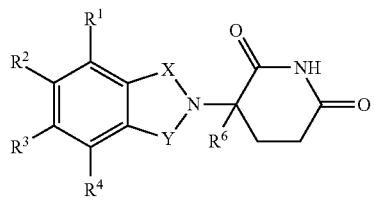

in which one of X and Y is C=O and the other of X and Y is C=O or $CH_2$;

each of $R^1$, $R^2$, $R^3$, and $R^4$, independently of the others, is halo, alkyl of 1 to 4 carbon atoms, or alkoxy of 1 to 4 carbon atoms or (ii) one of $R^1$, $R^2$, $R^3$, and $R^4$ is nitro or protected amino and the remaining of $R^1$, $R^2$, $R^3$, and $R^4$ are hydrogen; and $R^6$ is hydrogen, alkyl of 1 to 8 carbon atoms, benzo, chloro, or fluoro.

Other representative compounds are of formula:

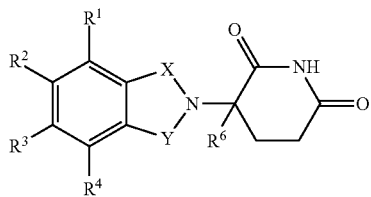

in which:
one of X and Y is C=O and the other of X and Y is C=O or CH$_2$;
(i) each of R$^1$, R$^2$, R$^3$, and R$^4$, independently of the others, is halo, alkyl of 1 to 4 carbon atoms, or alkoxy of 1 to 4 carbon atoms or (ii) one of R$^1$, R$^2$, R$^3$, and R$^4$ is —NHR$^5$ and the remaining of R$^1$, R$^2$, R$^3$, and R$^4$ are hydrogen;
R$^5$ is hydrogen, alkyl of 1 to 8 carbon atoms, or CO—R$^7$—CH(R$^{10}$)NR$^8$R$^9$ in which each of R$^7$, R$^8$, R$^9$, and R$^{10}$ is as herein defined; and
R$^6$ is alkyl of 1 to 8 carbon atoms, benzo, chloro, or fluoro.
Specific examples of the compounds are of formula:

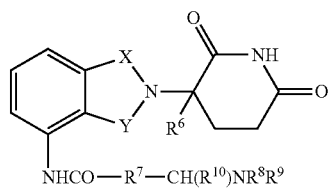

in which:
one of X and Y is C=O and the other of X and Y is C=O or CH$_2$;
R$^6$ is hydrogen, alkyl of 1 to 8 carbon atoms, benzyl, chloro, or fluoro;
R$^7$ is m-phenylene, p-phenylene or —(C$_n$H$_{2n}$)— in which n has a value of 0 to 4; each of R$^8$ and R$^9$ taken independently of the other is hydrogen or alkyl of 1 to 8 carbon atoms, or R$^8$ and R$^9$ taken together are tetramethylene, pentamethylene, hexamethylene, or —CH$_2$CH$_2$X$^1$CH$_2$CH$_2$— in which X$^1$ is —O—, —S— or —NH—; and
R$^{10}$ is hydrogen, alkyl of 1 to 8 carbon atoms, or phenyl.

Other specific immunomodulatory compounds include, but are not limited to, 1-oxo-2-(2,6-dioxo-3-fluoropiperidin-3-yl) isoindolines and 1,3-dioxo-2-(2,6-dioxo-3-fluoropiperidine-3-yl) isoindolines such as those described in U.S. Pat. Nos. 5,874,448 and 5,955,476, each of which is incorporated herein by reference. Representative compounds are of formula:

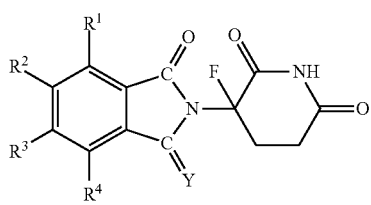

wherein:
Y is oxygen or H$^2$ and
each of R$^1$, R$^2$, R$^3$, and R$^4$, independently of the others, is hydrogen, halo, alkyl of 1 to 4 carbon atoms, alkoxy of 1 to 4 carbon atoms, or amino.

Other specific immunomodulatory compounds include, but are not limited to, the tetra substituted 2-(2,6-dioxopiperidin-3-yl)-1-oxoisoindolines described in U.S. Pat. No. 5,798,368, which is incorporated herein by reference. Representative compounds are of formula:

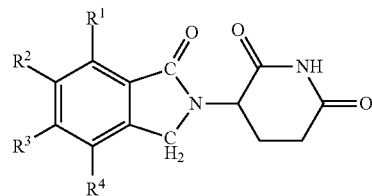

wherein each of R$^1$, R$^2$, R$^3$, and R$^4$, independently of the others, is halo, alkyl of 1 to 4 carbon atoms, or alkoxy of 1 to 4 carbon atoms.

Other specific immunomodulatory compounds include, but are not limited to, 1-oxo and 1,3-dioxo-2-(2,6-dioxopiperidin-3-yl) isoindolines disclosed in U.S. Pat. No. 6,403,613, which is incorporated herein by reference. Representative compounds are of formula:

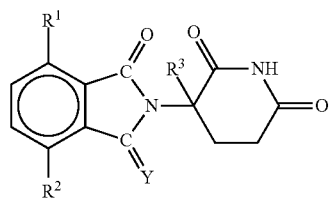

in which
Y is oxygen or H$_2$,
a first of R$^1$ and R$^2$ is halo, alkyl, alkoxy, alkylamino, dialkylamino, cyano, or carbamoyl, the second of R$^1$ and R$^2$, independently of the first, is hydrogen, halo, alkyl, alkoxy, alkylamino, dialkylamino, cyano, or carbamoyl, and
R$^3$ is hydrogen, alkyl, or benzyl.
Specific examples of the compounds are of formula:

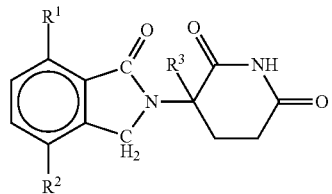

wherein
a first of R$^1$ and R$^2$ is halo, alkyl of from 1 to 4 carbon atoms, alkoxy of from 1 to 4 carbon atoms, dialkylamino in which each alkyl is of from 1 to 4 carbon atoms, cyano, or carbamoyl;
the second of R$^1$ and R$^2$, independently of the first, is hydrogen, halo, alkyl of from 1 to 4 carbon atoms, alkoxy of from 1 to 4 carbon atoms, alkylamino in which alkyl is of from 1 to 4 carbon atoms, dialkylamino in which each alkyl is of from 1 to 4 carbon atoms, cyano, or carbamoyl; and R³ is hydrogen, alkyl of from 1 to 4 carbon atoms, or benzyl. Specific examples include, but are not limited to, 1-oxo-2-(2,6-dioxopiperidin-3-yl)-4-methylisoindoline.

Other representative compounds are of formula:

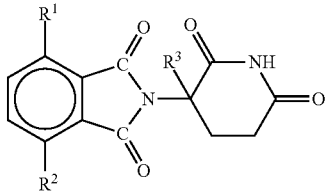

wherein:

a first of R¹ and R² is halo, alkyl of from 1 to 4 carbon atoms, alkoxy of from 1 to 4 carbon atoms, dialkylamino in which each alkyl is of from 1 to 4 carbon atoms, cyano, or carbamoyl;

the second of R¹ and R², independently of the first, is hydrogen, halo, alkyl of from 1 to 4 carbon atoms, alkoxy of from 1 to 4 carbon atoms, alkylamino in which alkyl is of from 1 to 4 carbon atoms, dialkylamino in which each alkyl is of from 1 to 4 carbon atoms, cyano, or carbamoyl; and R³ is hydrogen, alkyl of from 1 to 4 carbon atoms, or benzyl.

Other specific immunomodulatory compounds include, but are not limited to, 1-oxo and 1,3-dioxoisoindolines substituted in the 4- or 5-position of the indoline ring described in U.S. Pat. No. 6,380,239 and co-pending U.S. application publication no. 20060084815, published Apr. 20, 2006, which are incorporated herein by reference. Representative compounds are of formula:

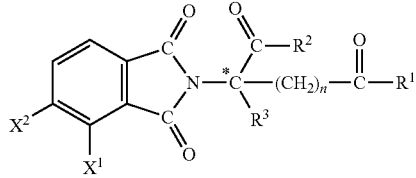

in which the carbon atom designated C* constitutes a center of chirality (when n is not zero and R¹ is not the same as R²); one of X¹ and X² is amino, nitro, alkyl of one to six carbons, or NH—Z, and the other of X¹ or X² is hydrogen; each of R¹ and R² independent of the other, is hydroxy or NH—Z; R³ is hydrogen, alkyl of one to six carbons, halo, or haloalkyl; Z is hydrogen, aryl, alkyl of one to six carbons, formyl, or acyl of one to six carbons; and n has a value of 0, 1, or 2; provided that if X¹ is amino, and n is 1 or 2, then R¹ and R² are not both hydroxy; and the salts thereof.

Further representative compounds are of formula:

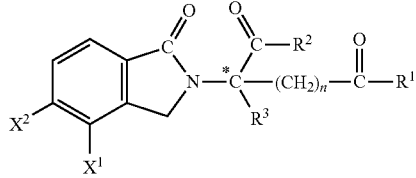

in which the carbon atom designated C* constitutes a center of chirality when n is not zero and R¹ is not R²; one of X¹ and X² is amino, nitro, alkyl of one to six carbons, or NH—Z, and the other of X¹ or X² is hydrogen; each of R¹ and R² independent of the other, is hydroxy or NH—Z; R³ is alkyl of one to six carbons, halo, or hydrogen; Z is hydrogen, aryl or an alkyl or acyl of one to six carbons; and n has a value of 0, 1, or 2.

Specific examples include, but are not limited to, 2-(4-amino-1-oxo-1,3-dihydro-isoindol-2-3-yl)-4-carbamoyl-butyric acid and 4-(4-amino-1-oxo-1,3-dihydro-isoindol-2-3-yl)-4-cabamoyl-butyric acid, which have the following structures, respectively, and pharmaceutically acceptable salts, solvates, prodrugs, and stereoisomers thereof:

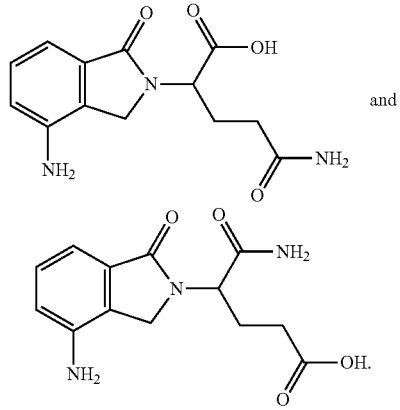

Other representative compounds are of formula:

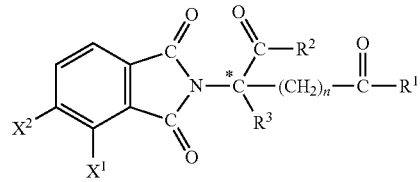

in which the carbon atom designated C* constitutes a center of chirality when n is not zero and R¹ is not R²; one of X¹ and X² is amino, nitro, alkyl of one to six carbons, or NH—Z, and the other of X¹ or X² is hydrogen; each of R¹ and R² independent of the other, is hydroxy or NH—Z; R³ is alkyl of one to six carbons, halo, or hydrogen; Z is hydrogen, aryl, or an alkyl or acyl of one to six carbons; and n has a value of 0, 1, or 2; and the salts thereof.

Specific examples include, but are not limited to, 4-carbamoyl-4-{4-[(furan-2-yl-methyl)-amino]-1,3-dioxo-1,3-dihydro-isoindol-2-yl}-butyric acid, 4-carbamoyl-2-{4-[(furan-2-yl-methyl)-amino]-1,3-dioxo-1,3-dihydro-isoindol-2-yl}-butyric acid, 2-{4-[(furan-2-yl-methyl)-amino]-1,3-dioxo-1,3-dihydro-isoindol-2-yl}-4-phenylcarbamoyl-butyric acid, and 2-{4-[(furan-2-yl-methyl)-amino]-1,3-dioxo-1,3-dihydro-isoindol-2-yl}-pentanedioic acid, which have the following structures, respectively, and pharmaceutically acceptable salts, solvate, prodrugs, and stereoisomers thereof:

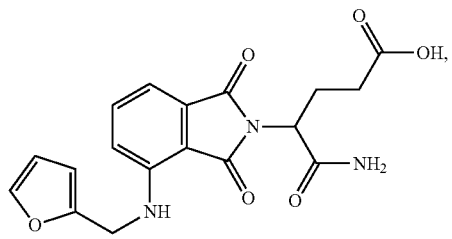

-continued

[Chemical structure: phthalimide with furfurylamino substituent, glutamine-like side chain with CONH2]

[Chemical structure: phthalimide with furfurylamino substituent, glutamic acid side chain with anilide], and

[Chemical structure: phthalimide with furfurylamino substituent, glutaric acid side chain]

Other specific examples of the compounds are of formula:

[Chemical structure of phthalimide derivative with X¹, X², R¹, R², R³ substituents and (CH₂)ₙ linker]

wherein:
one of $X^1$ and $X^2$ is nitro, or NH—Z, and the other of $X^1$ or $X^2$ is hydrogen;
each of $R^1$ and $R^2$, independent of the other, is hydroxy or NH—Z;
$R^3$ is alkyl of one to six carbons, halo, or hydrogen;
Z is hydrogen, phenyl, an acyl of one to six carbons, or an alkyl of one to six carbons; and
n has a value of 0, 1, or 2; and
if —COR² and —(CH₂)ₙCOR¹ are different, the carbon atom designated C* constitutes a center of chirality.

Other representative compounds are of formula:

[Chemical structure of phthalimide derivative with X¹, X², R¹, R², R³ substituents and (CH₂)ₙ linker]

wherein:
one of $X^1$ and $X^2$ is alkyl of one to six carbons;
each of $R^1$ and $R^2$, independent of the other, is hydroxy or NH—Z;
$R^3$ is alkyl of one to six carbons, halo, or hydrogen;
Z is hydrogen, phenyl, an acyl of one to six carbons, or an alkyl of one to six carbons; and
n has a value of 0, 1, or 2; and
if —COR² and —(CH₂)ₙCOR¹ are different, the carbon atom designated C* constitutes a center of chirality.

Still other specific immunomodulatory compounds include, but are not limited to, isoindoline-1-one and isoindoline-1,3-dione substituted in the 2-position with 2,6-dioxo-3-hydroxypiperidin-5-yl described in U.S. Pat. No. 6,458,810, which is incorporated herein by reference. Representative compounds are of formula:

[Chemical structure of isoindoline with 2,6-dioxo-3-hydroxypiperidin-5-yl substituent, with R¹, R² and X]

wherein:
the carbon atoms designated * constitute centers of chirality;
X is —C(O)— or —CH₂—;
$R^1$ is alkyl of 1 to 8 carbon atoms or —NHR³;
$R^2$ is hydrogen, alkyl of 1 to 8 carbon atoms, or halogen; and
$R^3$ is hydrogen,
  alkyl of 1 to 8 carbon atoms, unsubstituted or substituted with alkoxy of 1 to 8 carbon atoms, halo, amino, or alkylamino of 1 to 4 carbon atoms,
  cycloalkyl of 3 to 18 carbon atoms,
  phenyl, unsubstituted or substituted with alkyl of 1 to 8 carbon atoms, alkoxy of 1 to 8 carbon atoms, halo, amino, or alkylamino of 1 to 4 carbon atoms,
  benzyl, unsubstituted or substituted with alkyl of 1 to 8 carbon atoms, alkoxy of 1 to 8 carbon atoms, halo, amino, or alkylamino of 1 to 4 carbon atoms, or —COR⁴ in which
    $R^4$ is hydrogen,
    alkyl of 1 to 8 carbon atoms, unsubstituted or substituted with alkoxy of 1 to 8 carbon atoms, halo, amino, or alkylamino of 1 to 4 carbon atoms,
    cycloalkyl of 3 to 18 carbon atoms,
    phenyl, unsubstituted or substituted with alkyl of 1 to 8 carbon atoms, alkoxy of 1 to 8 carbon atoms, halo, amino, or alkylamino of 1 to 4 carbon atoms, or
    benzyl, unsubstituted or substituted with alkyl of 1 to 8 carbon atoms, alkoxy of 1 to 8 carbon atoms, halo, amino, or alkylamino of 1 to 4 carbon atoms.

All of the compounds described can either be commercially purchased or prepared according to the methods described in the patents or patent publications disclosed herein. Further, optically pure compounds can be asymmetrically synthesized or resolved using known resolving agents or chiral columns as well as other standard synthetic organic chemistry techniques.

Compounds used herein may be small organic molecules having a molecular weight less than about 1,000 g/mol, and are not proteins, peptides, oligonucleotides, oligosaccharides or other macromolecules.

It should be noted that if there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

Vitamin D Agents

Vitamin D agents suitable for the methods and compositions provided herein include, but are not limited to, vitamin D, calcitriol, 1α-hydroxy derivatives with a 17 side chain greater in length than the cholesterol or ergosterol side chains described, for example, in U.S. Pat. No. 4,717,721; cyclopentano-vitamin D analogs described, for example, in U.S. Pat. No. 4,851,401; vitamin $D_3$ analogues with alkynyl, alkenyl, and alkanyl side chains described, for example, in U.S. Pat. Nos. 4,866,048 and 5,145,846; trihydroxycalciferol described, for example, in U.S. Pat. No. 5,120,722; fluoro-cholecalciferol compounds described, for example, in U.S. Pat. No. 5,547,947; methyl substituted vitamin D described, for example, in U.S. Pat. No. 5,446,035; 23-oxa-derivatives described, for example, in U.S. Pat. No. 5,411,949; 19-nor-vitamin D compounds described, for example, in U.S. Pat. No. 5,237,110; and hydroxylated 24-homo-vitamin D derivatives described, for example, in U.S. Pat. No. 4,857,518. Examples include, but are not limited to, ROCALTROL (Roche Laboratories); CALCIJEX injectable calcitriol; seo-calcitol; 24a,26a,27a-trihomo-22,24-diene-1αa,25-(OH)-2-$D_3$; 20-epi-22-oxa-24a,26a,27a-trihomo-1α,25-(OH)-2-$D_3$, 1,25-$(OH)_2$-20-epi-$D_3$); calcipotriol, 1α,24s-$(OH)_2$-22-ene-26,27-dehydro-$D_3$,); drugs manufactured by Roche that include 1,25-$(OH)_2$-16-ene-$D_3$, 1,25-$(OH)_2$-16-ene-23-yne-$D_3$, and 25-$(OH)_2$-16-ene-23-yne-$D_3$; 22-oxacalcitriol (22-oxa-1α,25-(OH)-2-$D_3$) from Chugai; 1α-(OH)-$D_5$ from the University of Illinois; and drugs from the Institute of Medical Chemistry-Schering AG that include ZK 161422 (20-methyl-1,25-(OH)-2-$D_3$) and ZK 157202 (20-methyl-23-ene-1,25-(OH)-2-$D_3$); 1α-(OH)-$D_2$; 1α-(OH)-$D_3$ and 1α-(OH)-$D_4$.

In one embodiment, the vitamin D agent is vitamin D. In another embodiment, the vitamin D agent is 1α,25-dihydroxyvitamin $D_3$ (1,25 D3).

Methods of Administration

In all of the embodiments provided herein, appropriate doses and routes of the immunomodulatory compound and/or vitamin D agent may be determined depending on various factors. Such factors include, but are not limited to, the specific condition to be treated, the condition of the patient (including age and sex of the patient), prior treatments received by the patient, adverse effects observed, and/or any additional therapies used.

Administration of an immunomodulatory compound and a vitamin D agent to a patient can occur simultaneously or sequentially by the same or different routes of administration. The suitability of a particular route of administration employed for a particular active agent will depend on the active agent itself (e.g., whether it can be administered orally without decomposing prior to entering the blood stream) and the disease being treated. In one embodiment, the immunomodulatory compound provided herein is administered orally. In another embodiment, the vitamin D agent provided herein is administered orally. In another embodiment, both the immunomodulatory compound and vitamin D agent are administered orally. Typical routes of administration of the active agents or ingredients provided herein are known to those of ordinary skill in the art. See, e.g., *Physicians' Desk Reference*, (2006).

In one embodiment, an immunomodulatory compound provided herein is administered prior to the administration of a vitamin D agent provided herein. In another embodiment, an immunomodulatory compound provided herein is administered subsequent to the administration of a vitamin D agent provided herein. In another embodiment, an immunomodulatory compound provided herein is administered concurrently with a vitamin D agent provided herein, using the same or different routes of administration.

In another embodiment, an immunomodulatory compound is administered in an amount of from about 0.1 mg to about 150 mg/d in combination with a vitamin D agent to patients.

Also provided herein are methods of restoring vitamin D sensitivity, i.e., therapeutic efficacy of vitamin D agent, in a patient (e.g., a human) having cancer refractory to vitamin D treatments comprising administering an immunomodulatory compound provided herein, or a pharmaceutically acceptable salt, solvate, stereoisomer, or prodrug thereof. The method may be followed by administering a vitamin D agent subsequent to the treatment by an immunomodulatory compound to provide anti-cancer therapy.

In one embodiment, an immunomodulatory compound provided herein can be administered orally and daily in an amount of from about 0.1 to about 150 mg, from about 1 to about 50 mg, from about 1 to about 30 mg, from about 0.1 to about 30 mg, and from about 2 to about 25 mg prior to, during, or after the occurrence of the vitamin D resistance.

In one embodiment, an immunomodulatory compound provided herein can be administered orally and in single or divided daily doses in an amount of from about 0.10 to about 150 mg/day. In one embodiment, 4-(amino)-2-(2,6-dioxo(3-piperidyl))-isoindoline-1,3-dione may be administered in an amount of from about 0.1 to about 1 mg per day, or alternatively from about 0.1 to about 5 mg every other day. In another embodiment, 3-(4-amino-1-oxo-1,3-dihydro-isoindol-2-yl)-piperidine-2,6-dione may be administered in an amount of from about 1 to about 25 mg per day, or alternatively from about 10 to about 50 mg every other day.

In one embodiment, 4-(amino)-2-(2,6-dioxo(3-piperidyl))-isoindoline-1,3-dione may be administered in an amount of about 1, 2, or 5 mg per day to patients. In a particular embodiment, 3-(4-amino-1-oxo-1,3-dihydro-isoindol-2-yl)-piperidine-2,6-dione may be administered initially in an amount of 1 mg/day and the dose can be escalated every week to 10, 20, 25, 30 and 50 mg/day. In another embodiment, 3-(4-amino-1-oxo-1,3-dihydro-isoindol-2-yl)-piperidine-2,6-dione can be administered in an amount of up to about 30 mg/day to patients. In another embodiment, 3-(4-amino-1-oxo-1,3-dihydro-isoindol-2-yl)-piperidine-2,6-dione can be administered in an amount of up to about 40 mg/day to patients.

In one embodiment, 4-(amino)-2-(2,6-dioxo(3-piperidyl))-isoindoline-1,3-dione may be administered in an amount of from about 0.1 to about 1 mg per day, or alternatively from about 0.1 to about 5 mg every other day, to patients.

In another embodiment, 3-(4-amino-1-oxo-1,3-dihydro-isoindol-2-yl)-piperidine-2,6-dione may be administered in an amount of from about 1 to about 25 mg per day, or alternatively from about 10 to about 50 mg every other day, to patients.

In one embodiment, the vitamin D agent is administered orally, intravenously or subcutaneously and once or twice daily in an amount of from about 1 to about 1000 mg, from about 5 to about 500 mg, from about 10 to about 350 mg, or from about 50 to about 200 mg. The specific amount of the vitamin D agent will depend on the specific agent used, the type of disease being treated, prevented, or managed, the severity and stage of disease, and the amount(s) of immunomodulatory compounds used in combination, and any optional additional active agents concurrently administered to the patient.

In another embodiment, the vitamin D agent is 1α,25 D3. In another embodiment, the vitamin D agent is calcitriol. In another embodiment, the vitamin D agent is a vitamin $D_3$ analogue.

In one embodiment, the immunomodulatory compound is 3-(4-amino-1-oxo-1,3-dihydro-isoindol-2-yl)-piperidine-2,6-dione, and the vitamin D agent is 1α,25 D3. In another embodiment, the immunomodulatory compound is 4-(amino)-2-(2,6-dioxo(3-piperidyl))-isoindoline-1,3-dione, and the vitamin D agent is 1α,25 D3.

Examples of disorders treated, prevented or managed by immunomodulatory compounds in combination with vitamin D agents provided herein include, but are not limited to, various types of cancer. Examples of cancer and precancerous conditions include, but are not limited to, those described in U.S. Pat. Nos. 6,281,230 and 5,635,517 to Muller et al., in various U.S. patent publications to Zeldis, including Publ. Nos. 2004/0220144A1, published Nov. 4, 2004 (Treatment of Myelodysplastic Syndrome); 2004/0029832A1, published Feb. 12, 2004 (Treatment of Various Types of Cancer); and 2004/0087546, published May 6, 2004 (Treatment of Myeloproliferative Diseases). Examples also include those described in PCT/US04/14004, filed May 5, 2004. All of these references are incorporated herein in their entireties by reference.

Examples of specific cancer include, but are not limited to, cancers of the skin, such as melanoma; lymph node; breast; cervix; uterus; gastrointestinal tract; lung; ovary; prostate; colon; rectum; mouth; brain; head and neck; throat; testes; thyroid; kidney; pancreas; bone; spleen; liver; bladder; larynx; nasal passages; and AIDS-related cancers. The compounds provided here are useful for treating cancers of the blood and bone marrow, such as multiple myeloma and acute and chronic leukemias, for example, lymphoblastic, myelogenous, lymphocytic, and myelocytic leukemias. The compounds provided herein can be used for treating, preventing, or managing either primary or metastatic tumors.

Other examples of cancers include, but are not limited to, advanced malignancy, amyloidosis, neuroblastoma, meningioma, hemangiopericytoma, multiple brain metastase, glioblastoma multiforms, glioblastoma, brain stem glioma, poor prognosis malignant brain tumor, malignant glioma, recurrent malignant glioma, anaplastic astrocytoma, anaplastic oligodendroglioma, neuroendocrine tumor, rectal adenocarcinoma, Dukes C & D colorectal cancer, unresectable colorectal carcinoma, metastatic hepatocellular carcinoma, Kaposi's sarcoma, karotype acute myeloblastic leukemia, chronic lymphocytic leukemia (CLL), Hodgkin's lymphoma, non-Hodgkin's lymphoma, cutaneous T-Cell lymphoma, cutaneous B-Cell lymphoma, diffuse large B-Cell lymphoma, low grade follicular lymphoma, metastatic melanoma (localized melanoma, including, but not limited to, ocular melanoma), malignant mesothelioma, malignant pleural effusion mesothelioma syndrome, peritoneal carcinoma, papillary serous carcinoma, gynecologic sarcoma, soft tissue sarcoma, scleroderma, cutaneous vasculitis, Langerhans cell histiocytosis, leiomyosarcoma, fibrodysplasia ossificans progressive, hormone refractory prostate cancer, resected high-risk soft tissue sarcoma, unrescectable hepatocellular carcinoma, Waldenstrom's macroglobulinemia, smoldering myeloma, indolent myeloma, fallopian tube cancer, androgen independent prostate cancer, androgen dependent stage IV non-metastatic prostate cancer, hormone-insensitive prostate cancer, chemotherapy-insensitive prostate cancer, papillary thyroid carcinoma, follicular thyroid carcinoma, medullary thyroid carcinoma, and leiomyoma. In certain embodiments, the cancer is metastatic. In certain embodiments, the cancer is refractory or resistance to chemotherapy or radiation.

In another embodiment, provided herein are methods of treating, preventing or managing various forms of leukemias such as chronic lymphocytic leukemia, chronic myelocytic leukemia, acute lymphoblastic leukemia, acute myelogenous leukemia and acute myeloblastic leukemia, including leukemias that are relapsed, refractory or resistant, as disclosed in U.S. Publ. No. 2006/0030594, published Feb. 9, 2006, which is incorporated in its entirety by reference. The term "leukemia" refers malignant neoplasms of the blood-forming tissues. The leukemia includes, but is not limited to, chronic lymphocytic leukemia, chronic myelocytic leukemia, acute lymphoblastic leukemia, acute myelogenous leukemia and acute myeloblastic leukemia. The leukemia can be relapsed, refractory or resistant to conventional therapy. The term "relapsed" refers to a situation where patients who have had a remission of leukemia after therapy have a return of leukemia cells in the marrow and a decrease in normal blood cells. The term "refractory or resistant" refers to a circumstance where patients, even after intensive treatment, have residual leukemia cells in their marrow.

In yet another embodiment, provided herein are methods of treating, preventing or managing various types of lymphomas, including Non-Hodgkin's lymphoma (NHL). The term "lymphoma" refers a heterogenous group of neoplasms arising in the reticuloendothelial and lymphatic systems. "NHL" refers to malignant monoclonal proliferation of lymphoid cells in sites of the immune system, including lymph nodes, bone marrow, spleen, liver and gastrointestinal tract. Examples of NHL include, but are not limited to, mantle cell lymphoma, MCL, lymphocytic lymphoma of intermediate differentiation, intermediate lymphocytic lymphoma, ILL, diffuse poorly differentiated lymphocytic lymphoma, PDL, centrocytic lymphoma, diffuse small-cleaved cell lymphoma, DSCCL, follicular lymphoma, and any type of the mantle cell lymphomas that can be seen under the microscope (nodular, diffuse, blastic and mentle zone lymphoma).

In one embodiment, the cancer is breast cancer. In another embodiment, the cancer is prostate cancer.

Additional Active Agents

An immunomodulatory compound and a vitamin D agent can be used with or combined with other pharmacologically active compounds ("additional active agents or ingredients") in methods and compositions provided herein. It is believed that certain combinations work synergistically in the methods provided herein. Immunomodulatory compounds and/or vitamin D agents can also work to alleviate adverse effects associated with certain additional active agents, and some additional active agents can be used to alleviate adverse effects associated with immunomodulatory compounds and/or vitamin D agents provided herein.

One or more additional active ingredients or agents can be used in the methods and compositions provided herein together with an immunomodulatory compound and a vitamin D agent. Additional active agents can be large molecules (e.g., proteins) or small molecules (e.g., synthetic inorganic, organometallic, or organic molecules).

Examples of the additional active agents include, but are not limited to: semaxanib; cyclosporin; etanercept; doxycycline; bortezomib; acivicin; aclarubicin; acodazole hydrochloride; acronine; adozelesin; aldesleukin; altretamine; ambomycin; ametantrone acetate; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; celecoxib; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; ilmofosine; iproplatin; irinotecan; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; taxotere; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; and zorubicin hydrochloride.

Other additional agents include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; antidorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; capecitabine; carboxamide-amino-triazole; carboxamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol; dioxamycin; diphenyl spiromustine; docetaxel; docosanol; dolasetron; doxifluridine; doxorubicin; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imatinib (Gleevec®); imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mitoguazone; mitolactol; mitomycin analogues; mitonafide; mitotoxin fibroblast growth factor-saporin; mitoxantrone; mofarotene; molgramostim; Erbitux, human chorionic gonadotrophin; monophosphoryl lipid A+myobacterium cell wall sk; mopidamol; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; nilutamide; nisamycin; nitric oxide modulators; nitroxide antioxidant; nitrullyn; oblimersen (Genasense®); O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin;

prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stipiamide; stromelysin inhibitors; sulfinosine; superactive vasoactive intestinal peptide antagonist; suradista; suramin; swainsonine; tallimustine; tamoxifen methiodide; tauromustine; tazarotene; tecogalan sodium; tegafur; tellurapyrylium; telomerase inhibitors; temoporfin; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; velaresol; veramine; verdins; verteporfin; vinorelbine; vinxaltine; vitaxin; vorozole; zanoterone; zeniplatin; zilascorb; and zinostatin stimalamer.

Yet other additional active agents include, but are not limited to, 2-methoxyestradiol, telomestatin, inducers of apoptosis in mutiple myeloma cells (such as, for example, TRAIL), statins, semaxanib, cyclosporin, etanercept, doxycycline, bortezomib, oblimersen (Genasense®), remicade, docetaxel, celecoxib, melphalan, dexamethasone (Decadron®), steroids, gemcitabine, cisplatinum, temozolomide, etoposide, cyclophosphamide, temodar, carboplatin, procarbazine, gliadel, tamoxifen, topotecan, methotrexate, Arisa®, taxol, taxotere, fluorouracil, leucovorin, irinotecan, xeloda, CPT-11, interferon alpha, pegylated interferon alpha (e.g., PEG INTRON-A), capecitabine, cisplatin, thiotepa, fludarabine, carboplatin, liposomal daunorubicin, cytarabine, doxetaxol, pacilitaxel, vinblastine, IL-2, GM-CSF, dacarbazine, vinorelbine, zoledronic acid, palmitronate, biaxin, busulphan, prednisone, bisphosphonate, arsenic trioxide, vincristine, doxorubicin (Doxil®), paclitaxel, ganciclovir, adriamycin, estramustine sodium phosphate (Emcyt®), sulindac, and etoposide.

Cycling Therapy

In certain embodiments, the prophylactic or therapeutic agents disclosed herein are cyclically administered to a patient. Cycling therapy involves the administration of an active agent for a period of time, followed by a rest for a period of time, and repeating this sequential administration. Cycling therapy can reduce the development of resistance to one or more of the therapies, avoid or reduce the side effects of one of the therapies, and/or improves the efficacy of the treatment.

Consequently, in one embodiment, an immunomodulatory compound provided herein is administered daily in a single or divided doses in a four to six week cycle with a rest period of about a week or two weeks. In other embodiments, the frequency, number, and length of dosing cycles may be increased. Thus, also provided herein is the administration of an immunomodulatory compound for more cycles than are typical when it is administered alone.

In one embodiment, an immunomodulatory compound provided herein is administered daily and continuously for three or four weeks at a dose of from about 0.1 to about 150 mg/d, followed by a break of one or two weeks. 4-(Amino)-2-(2,6-dioxo(3-piperidyl))-isoindoline-1,3-dione is preferably administered daily and continuously at an initial dose of 0.1 to 5 mg/d with dose escalation (every week) by 1 to 10 mg/d to a maximum dose of 50 mg/d for as long as the therapy is tolerated. In a particular embodiment, 3-(4-amino-1-oxo-1,3-dihydro-isoindol-2-yl)-piperidine-2,6-dione is administered in an amount of about 1, 5, 10, or 25 mg/day, or in one embodiment, in an amount of about 10 mg/day, for three to four weeks, followed by one week or two weeks of rest in a four or six week cycle.

In one embodiment, an immunomodulatory compound provided herein and a vitamin D agent are administered orally, with administration of an immunomodulatory compound occurring 30 to 60 minutes prior to a vitamin D agent, during a cycle of four to six weeks. In another embodiment, the combination of an immunomodulatory compound provided herein and a vitamin D agent is administered by intravenous infusion over about 90 minutes every cycle. In one embodiment, one cycle comprises the administration of from about 1 to about 25 mg/day of 3-(4-amino-1-oxo-1,3-dihydro-isoindol-2-yl)-piperidine-2,6-dione and from about 1 to about 1000 mg/m$^2$/day of a vitamin D agent daily for three to four weeks and then one or two weeks of rest. In another embodiment, each cycle comprises the administration of from about 5 to about 10 mg/day of 4-(amino)-2-(2,6-dioxo(3-piperidyl))-isoindoline-1,3-dione and from about 1 to about 1000 mg/m$^2$/day of a vitamin D agent for 3 to 4 weeks followed by one or two weeks of rest. Typically, the number of cycles during which the combinatorial treatment is administered to a patient will be from about one to about 24 cycles, from about two to about 16 cycles, and from about four to about three cycles.

Pharmaceutical Compositions and Dosage Forms

Pharmaceutical compositions can be used in the preparation of individual, single unit dosage forms. Pharmaceutical compositions and dosage forms provided herein comprise an immunomodulatory compound provided herein, or a pharmaceutically acceptable salt, solvate (e.g., hydrate), stereoisomer, clathrate, or prodrug thereof, and a vitamin D agent provided herein. Pharmaceutical compositions and dosage forms provided herein can further comprise one or more excipients.

Pharmaceutical compositions and dosage forms provided herein can also comprise one or more additional active ingredients. Examples of optional second, or additional, active ingredients are disclosed herein.

Single unit dosage forms provided herein are suitable for oral, mucosal, parenteral (e.g., subcutaneous, intravenous, bolus injection, intramuscular, or intraarterial), topical, transdermal or transcutaneous administration to a patient. Examples of dosage forms include, but are not limited to: tablets; caplets; capsules, such as soft elastic gelatin capsules; cachets; troches; lozenges; dispersions; suppositories; powders; gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

The composition, shape, and type of dosage forms provided herein will typically vary depending on their use. For example, a dosage form used in the acute treatment of a disease may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease. These and other ways in which specific dosage forms encompassed herein will vary from one another will be readily apparent to those skilled in the art. See, e.g., *Remington's Pharmaceutical Sciences,* 20th ed., Mack Publishing, Easton Pa. (2000).

Typical pharmaceutical compositions and dosage forms comprise one or more excipients. Suitable excipients are well known to those skilled in the art of pharmacy, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets may contain excipients not suited for use in parenteral dosage forms. The suitability of a particular excipient may also depend on the specific active ingredients in the dosage form. For example, the decomposition of some active ingredients may be accelerated by some excipients such as lactose, or when exposed to water. Active ingredients that comprise primary or secondary amines are particularly susceptible to such accelerated decomposition. Consequently, the pharmaceutical compositions and dosage forms that contain little, if any, lactose other mono- or di-saccharides are provided in certain embodiments. As used herein, the term "lactose-free" means that the amount of lactose present, if any, is insufficient to substantially increase the degradation rate of an active ingredient.

Lactose-free compositions can comprise excipients that are well known in the art and are listed, for example, in the *U.S. Pharmacopeia* (USP) 25-NF20 (2002). In general, lactose-free compositions comprise active ingredients, a binder/filler, and a lubricant in pharmaceutically compatible and pharmaceutically acceptable amounts. In one embodiment, lactose-free dosage forms comprise active ingredients, microcrystalline cellulose, pre-gelatinized starch, and magnesium stearate.

Further encompassed are anhydrous pharmaceutical compositions and dosage forms comprising active ingredients, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, *Drug Stability: Principles & Practice,* 2d. Ed., Marcel Dekker, NY, N.Y., 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms provided herein can be prepared using anhydrous or low moisture containing ingredients and low moisture or low humidity conditions. Pharmaceutical compositions and dosage forms that comprise lactose and at least one active ingredient that comprises a primary or secondary amine are anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions are, for example, packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

Further provided are pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

Like the amounts and types of excipients, the amounts and specific types of active ingredients in a dosage form may differ depending on factors such as, but not limited to, the route by which it is to be administered to patients. In certain embodiment, the dosage forms comprise an immunomodulatory compound provided herein or a pharmaceutically acceptable salt, solvate (e.g., hydrate), stereoisomer, clathrate, or prodrug thereof in an amount of from about 0.10 to about 150 mg. In other embodiments, the dosage forms comprise an immunomodulatory compound provided herein or a pharmaceutically acceptable salt, solvate (e.g., hydrate), stereoisomer, clathrate, or prodrug thereof in an amount of about 0.1, 1, 2.5, 5, 7.5, 10, 12.5, 15, 17.5, 20, 25, 50, 100, 150 or 200 mg. In one embodiment, the dosage form comprises 3-(4-amino-1-oxo-1,3-dihydro-isoindol-2-yl)-piperidine-2,6-dione in an amount of about 1, 2.5, 5, 10, 15, 20, 25 or 50 mg. In certain embodiments, dosage forms comprise the second active ingredient in an amount of 1 to about 1000 mg, from about 5 to about 500 mg, from about 10 to about 350 mg, or from about 50 to about 200 mg. The specific amount of the second agent will depend on the specific agent used, the type of disease being treated or managed, and the amount(s) of an immunomodulatory compound provided herein and any optional additional active agents concurrently administered to the patient.

Oral Dosage Forms

Pharmaceutical compositions that are suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, *Remington's Pharmaceutical Sciences,* 20th ed., Mack Publishing, Easton Pa. (2000).

In one embodiment, the dosage form is a capsule or tablet comprising 3-(4-amino-1-oxo-1,3-dihydro-isoindol-2-yl)-piperidine-2,6-dione in an amount of about 1, 2.5, 5, 10, 15, 20, 25 or 50 mg and 1α,25 D3 in an amount of about 1, 10, 50, 100, 300, 500, or 1000 mg. In one embodiment, the capsule or tablet dosage form comprises 3-(4-amino-1-oxo-1,3-dihydro-isoindol-2-yl)-piperidine-2,6-dione in an amount of about 5 or 10 mg and 1α,25 D3 in an amount of about 1, 10, 50, 100, 300, 500, or 1000 mg.

In certain embodiment, the oral dosage forms provided herein are prepared by combining the active ingredients in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents.

Because of their ease of administration, tablets and capsules represent the most advantageous oral dosage unit forms, in which case solid excipients are employed. If desired, tablets can be coated by standard aqueous or nonaqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

Examples of excipients that can be used in oral dosage forms include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Suitable forms of microcrystalline cellulose include, but are not limited to, the materials sold as AVICEL-PH-101, AVICEL-PH-103 AVICEL RC-581, AVICEL-PH-105 (available from FMC Corporation, American Viscose Division, Avicel Sales, Marcus Hook, Pa.), and mixtures thereof. An specific binder is a mixture of microcrystalline cellulose and sodium carboxymethyl cellulose sold as AVICEL RC-581. Suitable anhydrous or low moisture excipients or additives include AVICEL-PH-103™ and Starch 1500 LM.

Examples of fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions is typically present in from about 50 to about 99 weight percent of the pharmaceutical composition or dosage form.

Disintegrants are used in the compositions to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms provided herein. The amount of disintegrant used varies based upon the type of formulation, and is readily discernible to those of ordinary skill in the art. Typical pharmaceutical compositions comprise from about 0.5 to about 15 weight percent of disintegrant or from about 1 to about 5 weight percent of disintegrant.

Disintegrants that can be used in pharmaceutical compositions and dosage forms include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums, and mixtures thereof.

Lubricants that can be used in pharmaceutical compositions and dosage forms include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL200, manufactured by W.R. Grace Co. of Baltimore, Md.), a coagulated aerosol of synthetic silica (marketed by Degussa Co. of Plano, Tex.), CAB-O-SIL (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

In certain embodiments, the solid oral dosage form comprises an immunomodulatory compound provided herein, anhydrous lactose, microcrystalline cellulose, polyvinylpyrrolidone, stearic acid, colloidal anhydrous silica, and gelatin.

5.3.2 Controlled Release Dosage Forms

Active ingredients provided herein can be administered by controlled release means or by delivery devices that are well known to those of ordinary skill in the art. Examples include, but are not limited to, those described in U.S. Pat. Nos. 3,845, 770; 3,916,899; 3,536,809; 3,598,123; and 4,008,719, 5,674, 533, 5,059,595, 5,591,767, 5,120,548, 5,073,543, 5,639,476, 5,354,556, 5,639,480, 5,733,566, 5,739,108, 5,891,474, 5,922,356, 5,972,891, 5,980,945, 5,993,855, 6,045,830, 6,087,324, 6,113,943, 6,197,350, 6,248,363, 6,264,970, 6,267,981, 6,376,461, 6,419,961, 6,589,548, 6,613,358, 6,699,500 and 6,740,634, each of which is incorporated herein by reference. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active ingredients provided herein. Thus provided herein are single unit dosage forms suitable for oral administration such as, but not limited to, tablets, capsules, gelcaps, and caplets that are adapted for controlled-release.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

In certain embodiments, the agent may be administered using intravenous infusion, an implantable osmotic pump, a transdermal patch, liposomes, or other modes of administration. In one embodiment, a pump may be used (see, Sefton, *CRC Crit. Ref. Biomed. Eng.* 14:201 (1987); Buchwald et al., *Surgery* 88:507 (1980); Saudek et al., *N. Engl. J. Med.* 321:574 (1989)). In another embodiment, polymeric materials can be used. In yet another embodiment, a controlled release system can be placed in a subject at an appropriate site determined by a practitioner of skill, i.e., thus requiring only a fraction of the systemic dose (see, e.g., Goodson, *Medical Applications of Controlled Release*, vol. 2, pp. 115-138 (1984)). Other controlled release systems are discussed in the review by Langer (*Science* 249:1527-1533 (1990)). The active ingredient can be dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The active ingredient then diffuses through the outer polymeric membrane in a release rate controlling step. The percentage of active ingredient in such parenteral compositions is highly dependent on the specific nature thereof, as well as the needs of the subject.

Parenteral Dosage Forms

Parenteral administration, generally characterized by injection, either subcutaneously, intramuscularly or intravenously is also contemplated herein. Injectables can be prepared in conventional forms, either as liquid solutions or suspensions, solid forms suitable for solution or suspension in liquid prior to injection, or as emulsions. Suitable excipients are, for example, water, saline, dextrose, glycerol or ethanol. In addition, if desired, the pharmaceutical compositions to be administered may also comprise minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins (see, U.S. Pat. No. 5,134,127).

Parenteral administration of the compositions includes intravenous, subcutaneous and intramuscular administrations. Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Pharmaceutically acceptable carriers, excipient or diluents used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations must be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylceluose, hydroxypropyl methylcellulose and polyvinylpyrrolidone. Emulsifying agents include Polysorbate 80 (TWEEN® 80). A sequestering or chelating agent of metal ions include EDTA. Pharmaceutical carriers also include ethyl alcohol, polyethylene glycol and propylene glycol for water miscible vehicles and sodium hydroxide, hydrochloric acid, citric acid or lactic acid for pH adjustment.

The concentration of an active ingredient is adjusted so that an injection provides an effective amount to produce the desired pharmacological effect. The exact dose depends on the age, weight and condition of the patient or animal as is known in the art.

The unit-dose parenteral preparations are packaged in an ampoule, a vial or a syringe with a needle. All preparations for parenteral administration must be sterile, as is known and practiced in the art.

Illustratively, intravenous or intraarterial infusion of a sterile aqueous solution comprising an active ingredient is an effective mode of administration. Another embodiment is a sterile aqueous or oily solution or suspension comprising an active material injected as necessary to produce the desired pharmacological effect.

Injectables are designed for local and systemic administration. Typically a therapeutically effective dosage is formulated to contain a concentration of at least about 0.1% w/w up to about 90% w/w or more or more than 1% w/w of an active ingredient to the treated tissue(s). The active ingredient may be administered at once, or may be divided into a number of smaller doses to be administered at intervals of time. It is understood that the precise dosage and duration of treatment is a function of the tissue being treated and may be determined empirically using known testing protocols or by extrapolation from in vivo or in vitro test data. It is to be noted that concentrations and dosage values may also vary with the age of the individual treated. It is to be further understood that for any particular subject, specific dosage regimens should be adjusted over time according to the individual need and the professional judgment of the person administering or supervising the administration of the formulations, and that the concentration ranges set forth herein are exemplary only and are not intended to limit the scope or practice of the claimed formulations.

The compound may be suspended in micronized or other suitable form or may be derivatized to produce a more soluble active product or to produce a prodrug. The form of the resulting mixture depends upon a number of factors, including the intended mode of administration and the solubility of the compound in the selected carrier or vehicle. The effective concentration is sufficient for ameliorating the symptoms of the condition and may be empirically determined.

Lyophilized Powders

Of interest herein are also lyophilized powders, which can be reconstituted for administration as solutions, emulsions and other mixtures. They may also be reconstituted and formulated as solids or gels.

The sterile, lyophilized powder is prepared by dissolving the active ingredient, or a pharmaceutically acceptable salt, solvate, hydrate or prodrug thereof, in a suitable solvent. The solvent may contain an excipient which improves the stability or other pharmacological component of the powder or reconstituted solution, prepared from the powder. Excipients that may be used include, but are not limited to, dextrose, sorbital, fructose, corn syrup, xylitol, glycerin, glucose, sucrose or other suitable agent. The solvent may also contain a buffer, such as citrate, sodium or potassium phosphate or other such buffer known to those of skill in the art at, typically, about neutral pH. Subsequent sterile filtration of the solution followed by lyophilization under standard conditions known to those of skill in the art provides the desired formulation. Generally, the resulting solution will be apportioned into vials for lyophilization. Each vial will contain a single dosage (10-1000 mg or 100-500 mg) or multiple dosages of the active ingredient. The lyophilized powder can be stored under appropriate conditions, such as at about 4° C. to room temperature.

Reconstitution of this lyophilized powder with water for injection provides a formulation for use in parenteral administration. For reconstitution, about 1-50 mg, 5-35 mg or about 9-30 mg of lyophilized powder, is added per mL of sterile water or other suitable carrier. The precise amount depends upon the compound used. Such amount can be empirically determined.

EXAMPLES

Certain embodiments provided herein are illustrated by the following non-limiting example.

Effects of Vitamin D on Breast Cancer Cells

Effects of a vitamin D agent on the growth of breast cancer cells were tested. MCF-12A, MCF7 and MDA-MB-231 are three variants of a breast cancer cell line with different tumorigenic potentials that were investigated. MCF-12A is non-malignant, MCF7 is malignant with normal p53 expression, and MDA-MB-231 is malignant with an abonormal p53 expression.

Cells were seeded in 24 wells plates at a density of $10^4$ cells per well and allowed to adhere for 24 hours. Dose responses were performed, testing increasing doses of 1α,25-dihydroxyvitamin $D_3$ (1,25 D3) (0, 1, 10, 50, 75 and 100 nM), over a period of 7 days. The drug was renewed every 2 days. Cell viability was then determined by neutral red assay, measuring absorbance at 550 nm.

As shown in FIG. 1, while MCF-12A and MCF7 showed sensitivity to vitamin D agent treatment, MDA-MB-231 was shown to be resistant to vitamin D agent treatment.

Effects of Immunomodulatory Compounds and Vitamin D on Breast Cancer Cells

Effects of 1-oxo-2-(2,6-dioxopiperidin-3-yl)-4-aminoisoindoline and 1,3-dioxo-2-(2,6-dioxopiperidin-3-3-yl)-4-aminoisoindoline, with or without vitamin D agent, on cell viability and cell growth of breast cancer cells were investigated. The cell lines used were MCF-12A, MCF7 and MDA-MB-231.

Cells were seeded in 24 wells plates at a density of $10^4$ cells per well and allowed to adhere for 24 hours. To determine the combination effects of the drugs, cells were treated with 100 nM 1,25 D3 and 10 nM 1-oxo-2-(2,6-dioxopiperidin-3-yl)-4-aminoisoindoline or 1,3-dioxo-2-(2,6-dioxopiperidin-3-3-yl)-4-aminoisoindoline. Each treatment was carried out for up to 7 days, but renewed every 2 days. Cell growth was then determined by Sulphorhodamine B (SRB) assay, measuring absorbance at 550 nm.

Figure 2A:
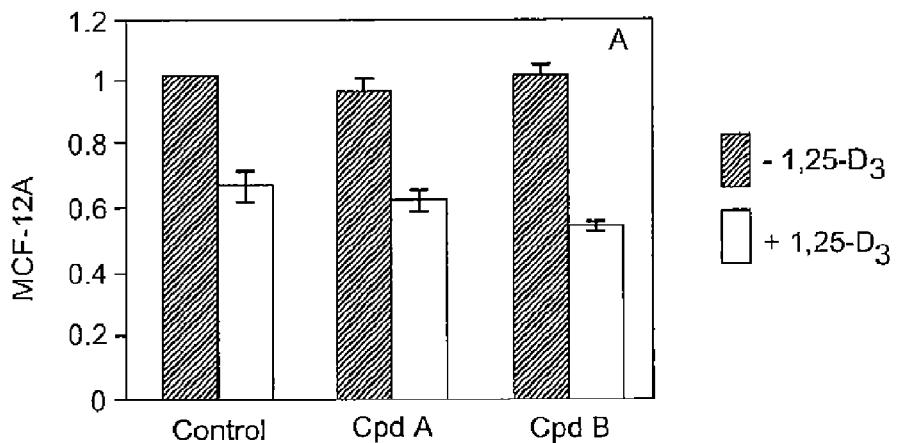
FIG. 2A illustrates effects of immunomodulatory compounds 1-oxo-2-(2,6-dioxopiperidin-3-3-yl)-4-aminoisoindoline and 1,3-dioxo-2-(2,6-dioxopiperidin-3-3-yl)-4-aminoisoindoline on cell viability and growth of MCF-12A, in the presence or absence of a vitamin D agent 1,25 D3.
Figure 2B:
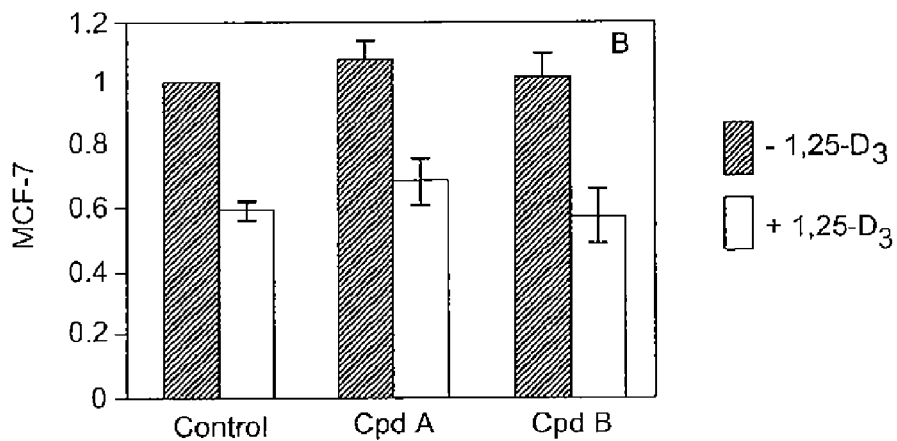
FIG. 2B illustrates effects of immunomodulatory compounds 1-oxo-2-(2,6-dioxopiperidin-3-3-yl)-4-aminoisoindoline and 1,3-dioxo-2-(2,6-dioxopiperidin-3-3-yl)-4-aminoisoindoline on cell viability and growth of MCF7, in the presence or absence of a vitamin D agent 1,25 D3.
Figure 2C:
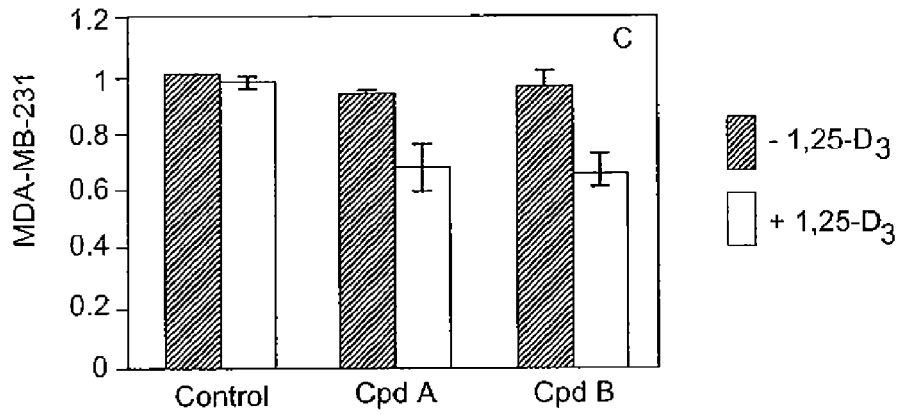
FIG. 2C illustrates effects of immunomodulatory compounds 1-oxo-2-(2,6-dioxopiperidin-3-3-yl)-4-aminoisoindoline and 1,3-dioxo-2-(2,6-dioxopiperidin-3-3-yl)-4-aminoisoindoline on cell viability and growth of MDA-MB-231, in the presence or absence of a vitamin D agent 1,25 D3.

As shown in FIGS. 2A and 2B, it was found that both immunomodulatory compounds do not significantly affect the cell viability and cell growth of MCF-12A or MCF7, in the presence or absence of vitamin D. As shown in FIG. 2C, however, with regard to MDA-MB-231 (i.e., vitamin D resistant cell line), while the immunomodulatory compounds did not affect the cell viability and cell growth of the cell line in the absence of vitamin D, it was demonstrated that the immunomodulatory compounds significantly increased (e.g., up to 50%) killing of the cells in the presence of vitamin D. The results indicate that immunomodulatory compounds may restore the vitamin D sensitivity in vitamin D resistant cells, resulting in increased killing of the cells in the presence of vitamin D.

Dose Determination

To assess the minimum doses of immunomodulatory compounds required for the synergistic effect with vitamin D on MDA-MB-231 cells, a dose response experiment was performed with 1-oxo-2-(2,6-dioxopiperidin-3-yl)-4-aminoisoindoline and 1,3-dioxo-2-(2,6-dioxopiperidin-3-yl)-4-aminoisoindoline, using a constant dose of 1,25 D3 (100 nM).

Cells were seeded in 24 wells plates at a density of $10^4$ cells per wekk and allowed to adhere for 24 hours. To determine the combination effects of the drugs, cells were treated with 100 nM 1,25 D3 and varying doses of 1-oxo-2-(2,6-dioxopiperidin-3-yl)-4-aminoisoindoline or 1,3-dioxo-2-(2,6-dioxopiperidin-3-yl)-4-aminoisoindoline. Each treatment was carried out for up to 7 days, but renewed every 2 days. Cell growth was then determined by Sulphorhodamine B (SRB) assay, measuring absorbance at 550 nm.

Figure 3:
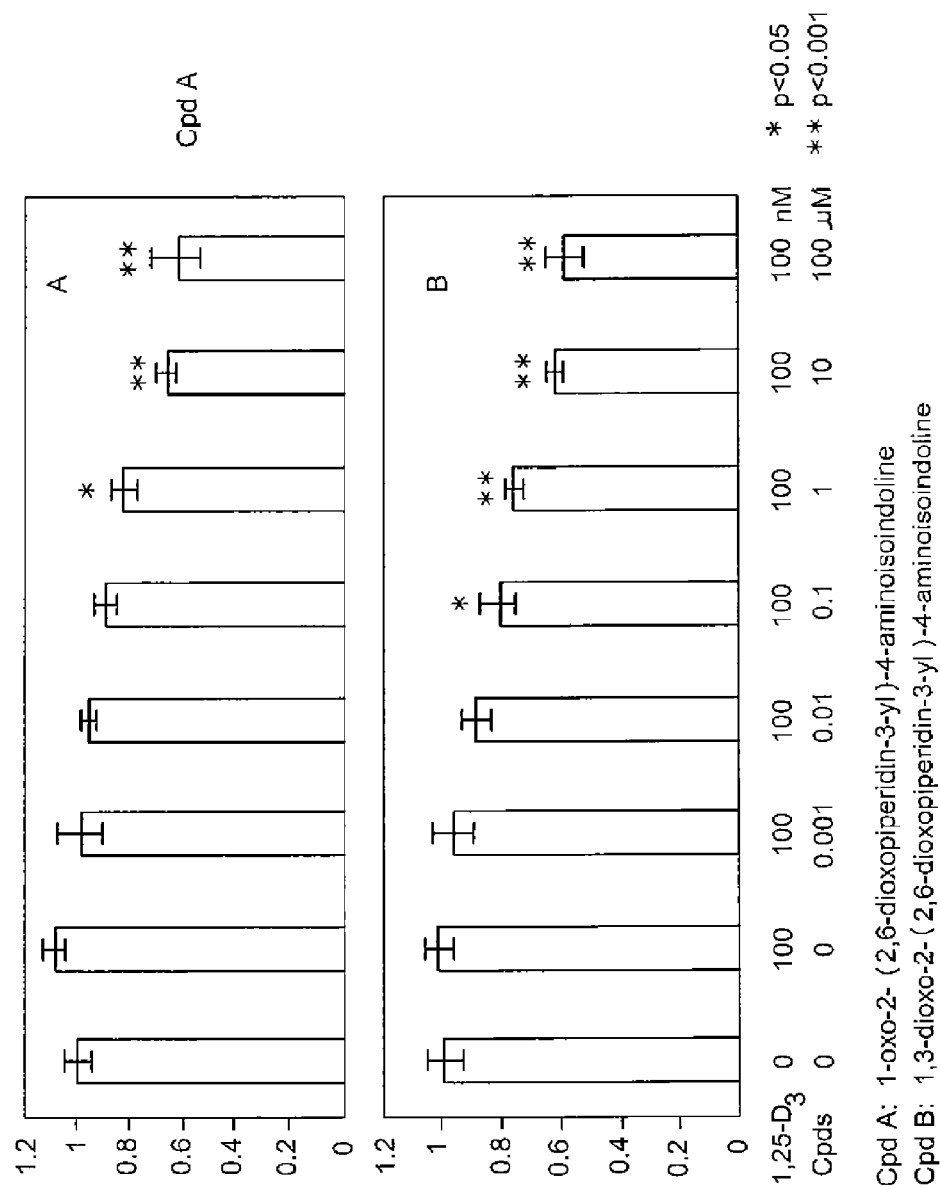
FIG. 3 illustrates the determination of minimum concentrations of 1-oxo-2-(2,6-dioxopiperidin-3-3-yl)-4-aminoisoindoline and 1,3-dioxo-2-(2,6-dioxopiperidin-3-3-yl)-4-aminoisoindoline that provide statistically significant cell growth inhibition in the presence of 100 nM 1,25 D3.

As shown in FIG. 3, there was statistically significant (using 1 way anova and post hoc analysis) inhibition of growth with a minimal concentration of 1 μM 1-oxo-2-(2,6-dioxopiperidin-3-yl)-4-aminoisoindoline (FIG. 3A) and 0.1 μM 1,3-dioxo-2-(2,6-dioxopiperidin-3-yl)-4-aminoisoindoline (FIG. 3B).

Effects of Combination on Apoptosis

To determine whether the inhibition of MDA-MB-231 cell growth and viability is due to an effect of the combination on apoptosis, the following assays were performed to measure apoptosis.

PARP Cleavage Assay

Cells were plated in 75 cm² flasks and cultured for 6 days with 1 µl/mL DMSO (control) or 1 µM 1-oxo-2-(2,6-dioxopiperidin-3-yl)-4-aminoisoindoline and 100 nM 1,25 D3, each alone or in combination. For each time point, medium was removed and cells were washed with ice-cold PBS. Cells were then lysed with RIPA buffer (1% NP40, 0.5% sodium deoxycholate, 0.1% SDS, PBS) and the lysate was centrifuged at 13000 rpm for 20 minutes at 4° C. The supernatant was collected and an aliquot taken for measuring protein concentration. The protein estimation was determined for each lysate using the Bio-Rad DC Protein Assay Kit according to the manufacturer's instructions. The protein extract was mixed with SDS (1/4), sonicated 10 seconds, and protein concentration was determined by Bradford assay.

SDS-polyacrylamide gel electrophoresis (SDS-PAGE) was run on a Mini Trans-Blot Module apparatus (Bio-Rad). The percentage of polyacrylamide/bis-acrylamide in the resolving gel in this experiment was 12% v/v. The following reagents were used for stacking gel: 0.67 mL 30% acrylamide/bis-acrylamide; 2.7 mL $H_2O$; 0.5 mL 1M trizma; 0.01 mL 10% ammonium persulfate; and 0.04 mL SDS. The following reagents were used for resolving gel: 3.3 mL 30% acrylamide/bis-acrylamide; 4 mL $H_2O$; 2.5 mL 1M trizma; 0.1 mL 10% ammonium persulfate; and 0.1 mL 10% SDS.

Once the resolving gel was prepared, polymerization was initiated by addition of 10 µl N',N',N',N'-teramethylethylenediamine (TEMED). Lysates were boiled for 5 minutes and chilled on ice then loaded into the stacking gel, with volumes adjusted so that equal amounts of protein were loaded. Rainbow colored markers (Sigma Aldrich) were also added in one well to monitor the electrophoretic solution. Electrophoresis was performed at 40 mA constant current for 1 to 2 hours in running buffer (10×25 mM trizma, 192 mM glycine, 0.1% SDS).

For western blotting, the proteins were transferred from the gel onto Hybond C-Super nitrocellulose membrane (Amersham International, U.K.) in a Mini Trans-Blot apparatus (Bio-Rad) according to the manufacturer's instructions. Transfer was performed at 100 V for 1.5 to 2 hours in transfer buffer (25 mM Tris base, 192 mM glycine, 20% methanol, pH 8.2). The nitrocellulose was blocked after 1 hour with milk solution (PBS 1×, 1% Tween 20, 1% Triton X100, 5% fat-free milk). The membrane was then stained for 1 hour with the primary antibodies Total-PARP and Cleaved-PARP in the milk solution. The membrane was washed with milk solution and stained with secondary antibody (anti-rabbit from Sigma Aldrich) for 1 hour. Finally, the membrane was washed in PBS+1% Tween 20+1% Triton X100, washed again with PBS 1× and revealed with the enhanced chemiluminescence (ECL) detection agent (Amersham International, U.K.). The membrane was then wrapper in cling-film and placed in a cassette and, in the dark, pieces of autography film (GRI) were placed over it and left for the desired time before being put through a developer.

Figure 4:
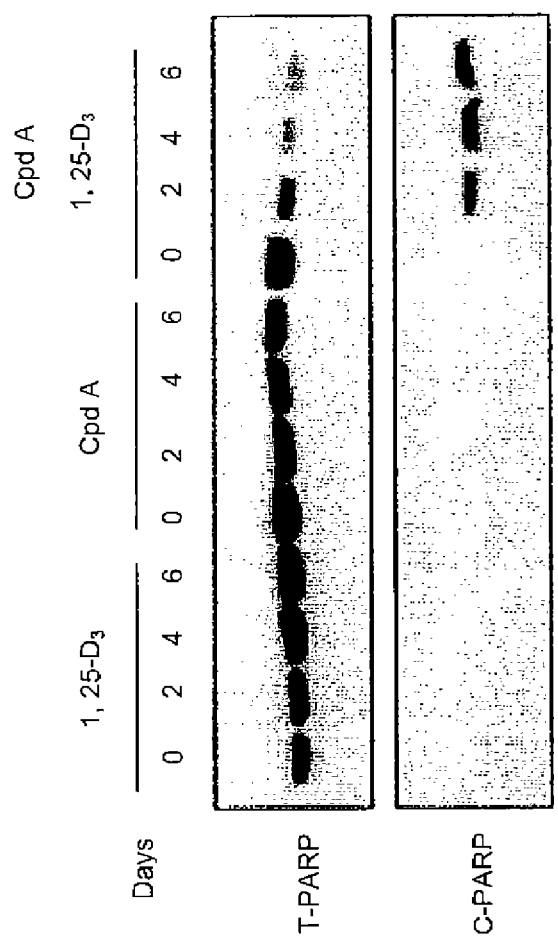
FIG. 4 illustrates the results of PARP cleavage tests performed on cells treated with 1,25 D3 alone, 1-oxo-2-(2,6-dioxopiperidin-3-yl)-4-aminoisoindoline alone, or 1,25 D3 and 1-oxo-2-(2,6-dioxopiperidin-3-3-yl)-4-aminoisoindoline in combination.

As shown in FIG. 4, it was shown that there was no PARP cleavage in cells treated with vitamin D or 1-oxo-2-(2,6-dioxopiperidin-3-yl)-4-aminoisoindoline alone, i. e., no signals seen with the cleaved PARP antibody, but significant level of cleaved PARP was observed in connection with the combination. These results indicate that the combination has a marked effect on apoptosis.

Annexin V/P.I. Staining

Cells were seeded into 6 well plates at a density of 2×10⁶ cells/well. Cells were treated with 1 µl/mL DMSO (control) or 1 nM 1-oxo-2-(2,6-dioxopiperidin-3-yl)-4-aminoisoindoline and 100 nM 1,25 D3, each alone or in combination for up to 6 days. Medium was removed by EDTA treatment, and cells were washed twice with ice-cold PBS. Cells were then resuspended into the buffer at a dilution of 1×10⁶ cells/mL. 10⁵ cells were then stained with Annexin V and Propidium Iodide ("PI"). Staining was analyzed by FACS. Results were expressed as the percentage of control Annexin V or PI staining where the control was cells treated with DMSO only. Results were from triplicate wells.

As shown in FIG. 5, it was shown that there is no significant increase in apoptosis in cells treated with vitamin D or 1-oxo-2-(2,6-dioxopiperidin-3-yl)-4-aminoisoindoline alone as assessed by either Annexin V or PI staining. However, a significant increase in apoptosis was observed in cells treated with the combination as assessed by both Annexin V and PI staining. These results also suggest that the combination has a marked effect on apoptosis.

Lenalidomide Restores a Vitamin D Sensitive Phenotype to the Vitamin D Resistant Breast Cancer Cells MDA-MB-231 Through Inhibition of BCL-2

Vitamin D has been well established as an essential component involved in skeletal health. The active hormonal metabolite of vitamin D is, 1α, 25-dihydroxyvitamin D3 (1,25 $D_3$) which is synthesized in the kidney and mediates the provision of mineral for bone by the stimulation of intestinal absorption of calcium and phosphate (Holick M F. Resurrection of vitamin D deficiency and ricket. *J Clin Invest.* 2006). Following the cloning of the receptor for vitamin D in 1987, receptors for vitamin D were discovered in many tissues including breast, where levels of the receptor were shown to rise upon lactation (Zinser, G. M. et al. *Mol Endocrinol* 18, 2208-2223 (2004)). The circulating levels of 1,25 $D_3$ also rise in pregnancy and vitamin D is thought to play a role in mammary gland differentiation and lactation. It has also been shown that the VDR is expressed in over 80% of breast cancer biopsies and that an increased level of expression of VDR in breast tumours correlates with disease free survival (Friedrich, M. et al. *Histochem. J* 34, 35-40 (2002), Friedrich, M. *Clin Exp. Obstet. Gynecol.* 27, 77-82 (2000), Friedrich, M. et al. *Histochem. J Cytochem.* 46, 1335-1337 (1998), and Friedrich, M. et al. *Anticancer Res.* 26, 2615-2620 (2006)). The role of 1,25 $D_3$ in prevention of breast cancer was demonstrated in mammary tumours of mice arising from 7,12-dimethylbenz(a)-anthracene (DMBA) injection, where prior treatment with the drug inhibited the development of tumours in the mice (Guyton, K. Z. et al. *Annual Review of Pharmacology and Toxicology* 41, 421-442 (2001)). Further studies have demonstrated the ability of 1,25 $D_3$ to inhibit breast tumour growth both in-vitro and in-vivo. Effects on tumour cells in-vitro (on an amelanotic melanoma line) were first demonstrated in 1981, followed by reports on inhibition of growth and differentiation of many other cell lines including breast cancer lines over the last 20 years (Colston, K. W. et al. *Endocr. Relat Cancer* 9, 45-49 (2002)). The inhibitory effects of 1,25 $D_3$ on breast cancer cell lines are thought to be through a regulation of the cell cycle, with effects on several cell cycle regulators such as increases in cyclin dependant kinase inhibitors and the pro-apoptotic protein P21 as seen in the cell line MCF-7 (Verlinden, L. et al. *Mol. Cell. Endocrinol.* 142, 57-65 (1998)). There is also an induction of apoptosis with loss of the anti-apoptotic molecule BCL2, but effects are not mediated by caspases or P53 (Mathiasen, I. S. et al. *Cancer Res.* 59, 4848-4856 (1999)).

Vitamin D has also been shown to be a promising clinical agent in both prevention and treatment of breast cancer (Colston K W et al. Possible role for vitamin D in controlling breast cancer cell proliferation. *Lancet.* 1989). Vitamin D has also been shown to be a promising clinical agent in both prevention and treatment of and other cancers including prostate cancer and multiple myeloma (Trump, D. L. et al. *Anticancer Research* 26, 2551-2556 (2006)). Phase 1 trials in refractory cancers have shown promising results. The two major caveats with these studies have been the hypercalcaemia caused by vitamin D and the resistance to vitamin D that develops or is present in many breast cancer patients (Byrne, B. et al. *J Steroid Biochem. Mol. Biol.* 103, 703-707 (2007) and Welsh, J. *J Bone Miner. Res.* 22 Suppl 2, V86-V90 (2007)). The problem of resistance (both inherent and induced) to the drug is very common although 1,25 $D_3$ treatment of breast cancer cell lines is extremely effective with IC50 values in the nM region (Colston, K. W. et al. *Endocr. Relat Cancer* 9, 45-49 (2002) and Colston, K. W. et al. *Biochem Pharmacol.* 44, 693-702 (1992)). A number of breast cancer cell lines that express VDR fail to respond to the anti-proliferative effects of 1,25(OH)$_2$D$_3$ (Byrne, B. et al. *J Steroid Biochem. Mol. Biol.* 103, 703-707 (2007)). Data from mammary cell lines suggest that oncogenic transformation with SV40 or ras inhibits VDR signalling and induces resistance to the growth inhibitory effects of 1,25 $D_3$ and therefore breast cancer progression is predicted to lead to a loss of sensitivity to 1,25 $D_3$ (Kemmis, C. M. et al. *J Cell Biochem.* 105, 980-988 (2008)). Agents that can reverse the resistance of refractory tumours to vitamin D are therefore important in any anti-cancer therapy using vitamin D (Galustian C et al. The anti-cancer agents lenalidomide and pomalidomide inhibit the proliferation and function of T regulatory cells. *Cancer Immunol Immunother.* 2009). The immunomodulatory drug lenalidomide, has been previously shown to have proapoptotic effects in several tumour cell lines and has been reported to overcome drug resistance in myeloma cell lines and primary patient cells, where growth arrest and apoptosis is induced (Mitsiades, N. et al. *Blood* 99, 4525-4530 (2002)). Its proapoptotic mechanisms include effects on caspases, and inhibition of the anti-apoptotic molecule BCL-2 (Quach, H. et al. *Leukemia* 24, 22-32 (2010)). Lenalidomide (CC-503) also has numerous other anti-cancer properties, such as inhibitory effects on invasion, metastasis, angiogenesis in addition to immunomodulatory effects that enhance NK and T cell function, and inhibit T regulatory cell numbers and function (Galustian, C. et al. *Expert Opin. Pharmacother.* 10, 125-133 (2009), Galustian, C. et al. *Cancer Immunol. Immunother.* 58, 1033-1045 (2009), and Liu, W. M. et al. *Br. J. Cancer* 101, 803-812 (2009))

In this study, we investigated whether the drug lenalidomide would confer vitamin D sensitivity to a vitamin D resistant breast cancer cell line MDA-MB-231. This cell line has been established as being refractory to vitamin D, although it expresses vitamin D receptors. The mechanisms of resistance to vitamin D in MDA-MB-231 cells are not yet understood, but resistance is reversed by the use of agents directly affecting apoptosis such as genestein and BCL2 inhibitors (Li, Z. et al. *Toxicol. In Vitro* 22, 1749-1753 (2008)). We therefore deduced that lenalidomide, which can target a number of proteins in the cell growth and apoptotic pathway and can sensitize multiple myeloma cells to a number of chemotherapeutic agents, would also be able to sensitise the cell line to vitamin D. We now demonstrate that lenalidomide can indeed reverse the resistance of the MDA-MB-231 cell line to 1,25 $D_3$, and the addition of both agents has a super additive effect on apoptosis as measured by parp cleavage, and annexin V expression on the cells. We show that the restoration of sensitivity is through a change in the expression of pro-apoptotic and anti-apoptotic molecules, and that the most significant changes is the inhibition of BCL-2 expression in the presence of the two drugs.

Materials and Methods

Cell Culture and Reagents

The malignant MCF-7, MCF-7/VD$^R$, HBL-100 and MDA-MB-231 cells were grown in RPMI 1640 supplemented with 2 mM of glutamine, 100 IU/ml of penicillin, 100 µg/ml of streptomycin and 10% of FBS. MCF-12A were grown in DMEM/F12 supplemented with 2 mM of glutamine, 100 IU/ml of penicillin, 100 µg/ml of streptomycin, 5% horse serum, 100 ng/ml of cholera toxin, 20 ng/ml of epidermal growth factor, 0.01 mg/ml of insulin and 500 ng/ml of hydrocortisone. 1, 25 dihydroxyvitamin $D_3$ (Sigma Aldrich, UK) was used at a concentration of 100 nM. Lenalidomide (CC-5013), pomalidomide (CC-4047) and thalidomide (Celgene) were used at different concentrations for up to 100 nM. ABT-263 was purchased from Genentech and was used at different concentrations up to 20 µM. DMSO was used as vehicle.

Growth Assay

After 6 days treatment, cells were seeded in 24 well plates at a density of 1×10$^4$ cells/well. After 24 h cells were treated with reagents or vehicle for up to six days. Cells were treated for up to 6 days with log doses of Thalidomide (0.1 µM up to 100 µM), pomalidomide and lenalidomide (0 µM up to 10 µM). At the end of each experiment, cells were fixed to the bottom of the well by addition of ice-cold 50% w/v trichloroacetic acid (TCA) to give a final concentration of 10% TCA. Plates were incubated at 4° C. for 30 minutes and then washed with distilled water. Plates were allowed to air-dry at room temperature before staining with 0.4% w/v SRB in 1% v/v acetic acid and incubated for 15 minutes on a shaker. The plates were then extensively washed with 1% acetic acid to remove unbound dye and were again allowed to air-dry at room temperature. Incorporated dye was solubilised with 200 µl 10 nM Tris base. 100 µl aliquots were transferred to a 96 well plate and absorbance at 550 nm was determined Viability Assay After 6 days treatment, cells were seeded into 24 well plates at a density of 1×10$^4$ cells/wells. After 24 h, cells were treated with reagents or vehicle for up to six days. At the end of the incubation period, medium was removed and cells were incubated with neutral red solution (40 µg/ml in phenol red and serum free DMEM) for 2 h at 37° C. After removal of the neutral red solution, wells were rinsed once with 1 ml 4% formal saline containing 0.5% CaCl$_2$. Plates were inverted on paper towel to drain and 200 µl of elution fluid (1% acetic acid in 50% ethanol) was added. Following incubation at room temperature for 30 min with gentle shaking, absorbance at 550 nm was determined Western Blot Analysis Cells were lysed in RIPA buffer containing 1% NP40, 0.5% sodium deoxycholate, 0.1% SDS, PBS. Equal amounts of protein (20 µg per lane) were subjected to SDS-PAGE and transferred to nitrocellulose membranes. Membranes were blocked with 5% milk in 0.05% Tween-20/TBS and then incubated with the first antibody in 0.5% milk overnight. Membranes were then incubated with the secondary anti-mouse or anti-rabbit horseradish peroxidase conjugated antibody. Bands were visualised using the enhanced chemiluminescence Western blotting detection system (ECL, Amersham, N.J., USA). Densitometric analysis was performed using Adobe Photoshop CS2. Anti-cleaved PARP and anti-total PARP antibodies (New England biolab, Cell Signalling), were used at a dilution of 1/1000 and anti-rabbit (AbCam, UK), at a dilution of 1/5000.

FACS Analysis

To assess the nature of MDA-MB-231 cell death (apoptosis or necrosis) induced by co-treatment of lenalidomide/1, 25-$D_3$ cells were seeded into 25 cm2 flasks at a density of $2 \times 10^6$ cells/flask. Cells were treated with 1 µl/mL DMSO (control), 1 µM lenalidomide (CC-503) or 100 nM 1,25-$D_3$ alone or in combination for up to 6 days. Medium was removed by EDTA treatment and cells were washed twice with ice-cold PBS. Cells were then resuspended into the buffer at a dilution of $1 \times 10^6$ cells/ml. $10^5$ cells were then stained with Annexin V and Iodure Propidium. Staining was analysed by FACS.

Protein Array

MDA-MB-231 cells were treated with 1 nM lenalidomide with or without 100 nM 1,25-$D_3$ for up to 6 days. Cells were lysed in RIPA buffer containing 1% NP40, 0.5% sodium deoxycholate, 0.1% SDS and PBS and lysates containing 300 µg protein were probed with an R and D apoptosis protein array kit according to the manufacturers instructions (R&D catalogue number ARY009). Spots were visualised using the enhanced chemiluminescence Western blotting detection system (ECL, Amersham, N.J., USA). Densitometric analysis was performed using Adobe Photoshop CS2.

Results

Single Agent IMiDs Thalidomide, Lenalidomide and Pomalidomide do not Affect Cell Viability or Growth in MCF-7, MCF-12a or MDA-MB-231 Cell Lines.

Figure 6A:
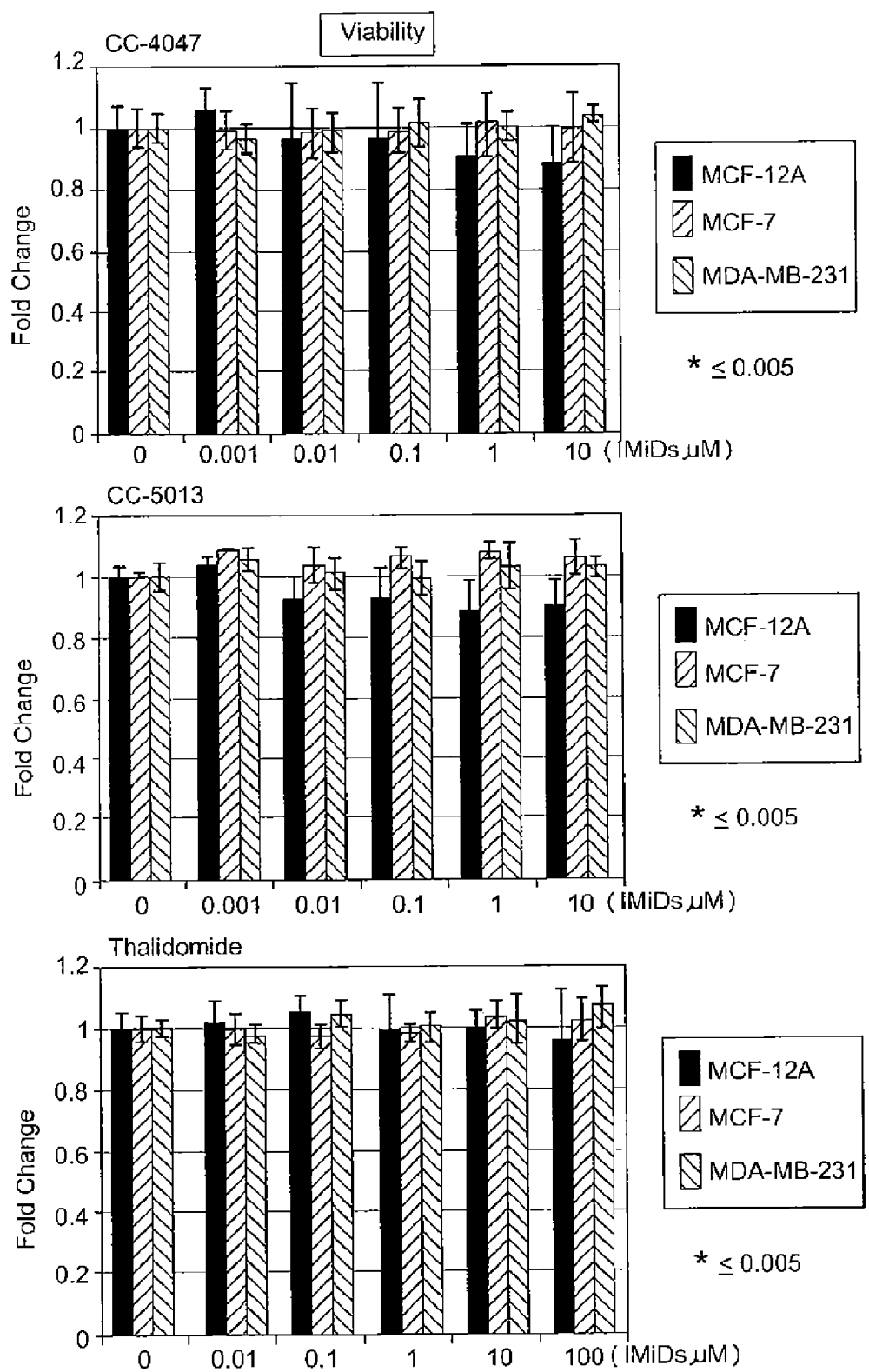
FIG. 6 illustrates the effects of IMiDs treatment on breast cancer cell growth and viability.
Figure 6B:
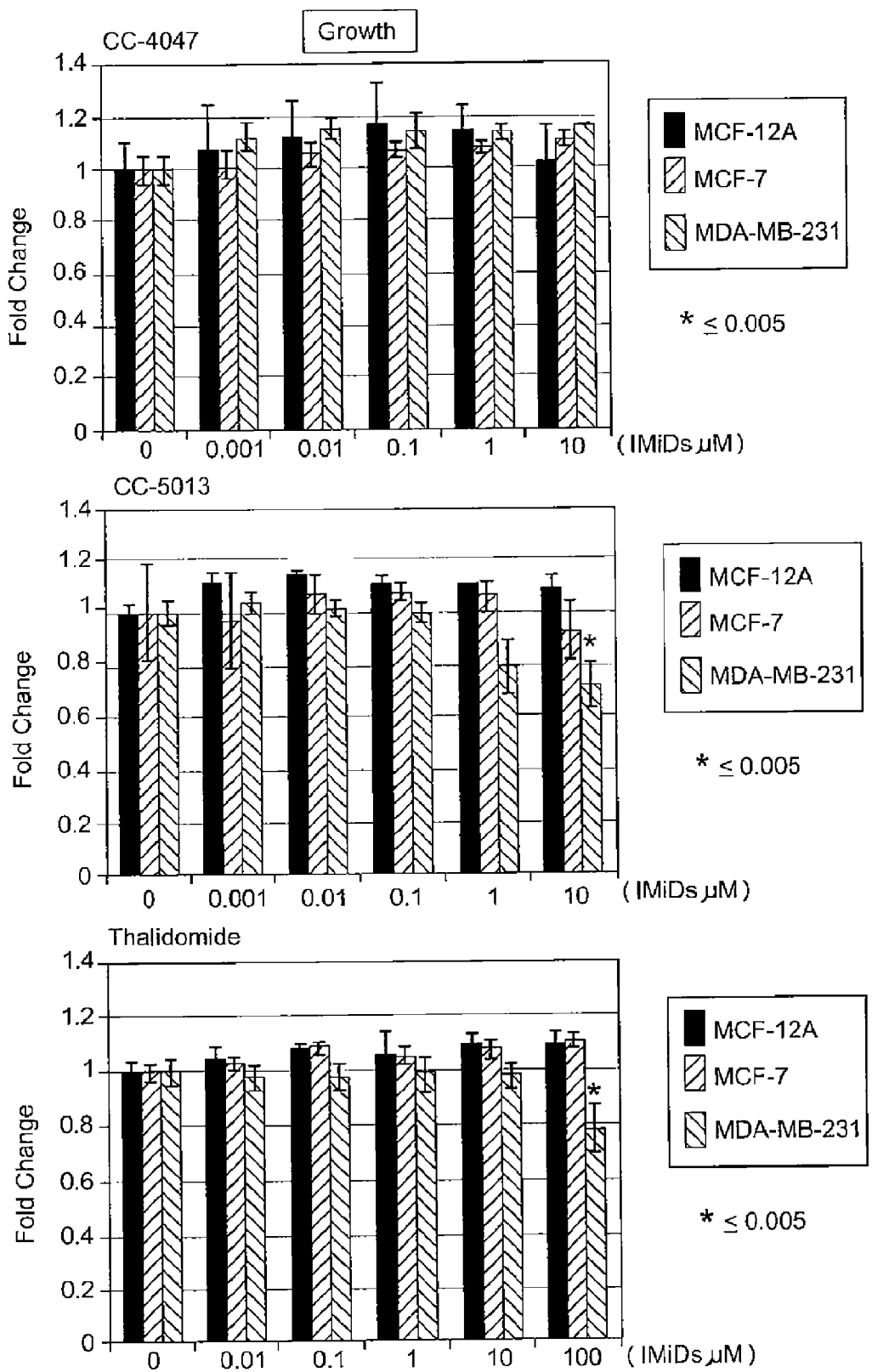

We first investigated the effects of single agent IMiDs thalidomide, lenalidomide or pomalidomide on the viability and growth of MCF-12A, MCF-7 and MDA-MB-231 breast cancer cell lines. FIG. 6 illustrates the effects of IMiDs treatment on breast cancer cell growth and viability. MCF-12A, MCF-7 and MDA-MB-231 cells were treated for up to 6 days with increasing doses of Thalidomide (0.01 µM up to 100 µM), CC-4047 and lenalidomide (0.001 µM up to 10 µM). (6A) illustrates cell viability was measured by neutral red dye assay. (6B) Cell growth was estimated by SRB assay. *($p<0.005$ by 1 way anova and Newman Keuls post test). Statistics have been performed comparing the significance between control (non-treated cells) and treated cells. None of the IMiDs alone had effects on the viability of the 3 breast cancer cell lines as measured by the neutral red assay (6A). MCF-12A and MCF-7 cells were insensitive to growth inhibition by IMiD treatment ($p>0.05$) (illustrated in 6B). Lenalidomide and Thalidomide treatment led to a small inhibition of growth of MDA-MB-231 cells (28% and 20% respectively; $p<0.05$) but only at the highest doses of drug (10 µM lenalidomide and 100 µM Thalidomide). Pomalidomide had no effects on MDA-MB-231 cell growth ($p>0.05$). These results show that growth and viability of MCF-12A, MCF-7 and MDA-MB-231 are not effected by single agent IMiDS used at physiological doses.

Effects of Co-Treatment with IMiDs/1, 25-$D_3$ on Different Breast Cell Growth and Viability.

Figure 7A:
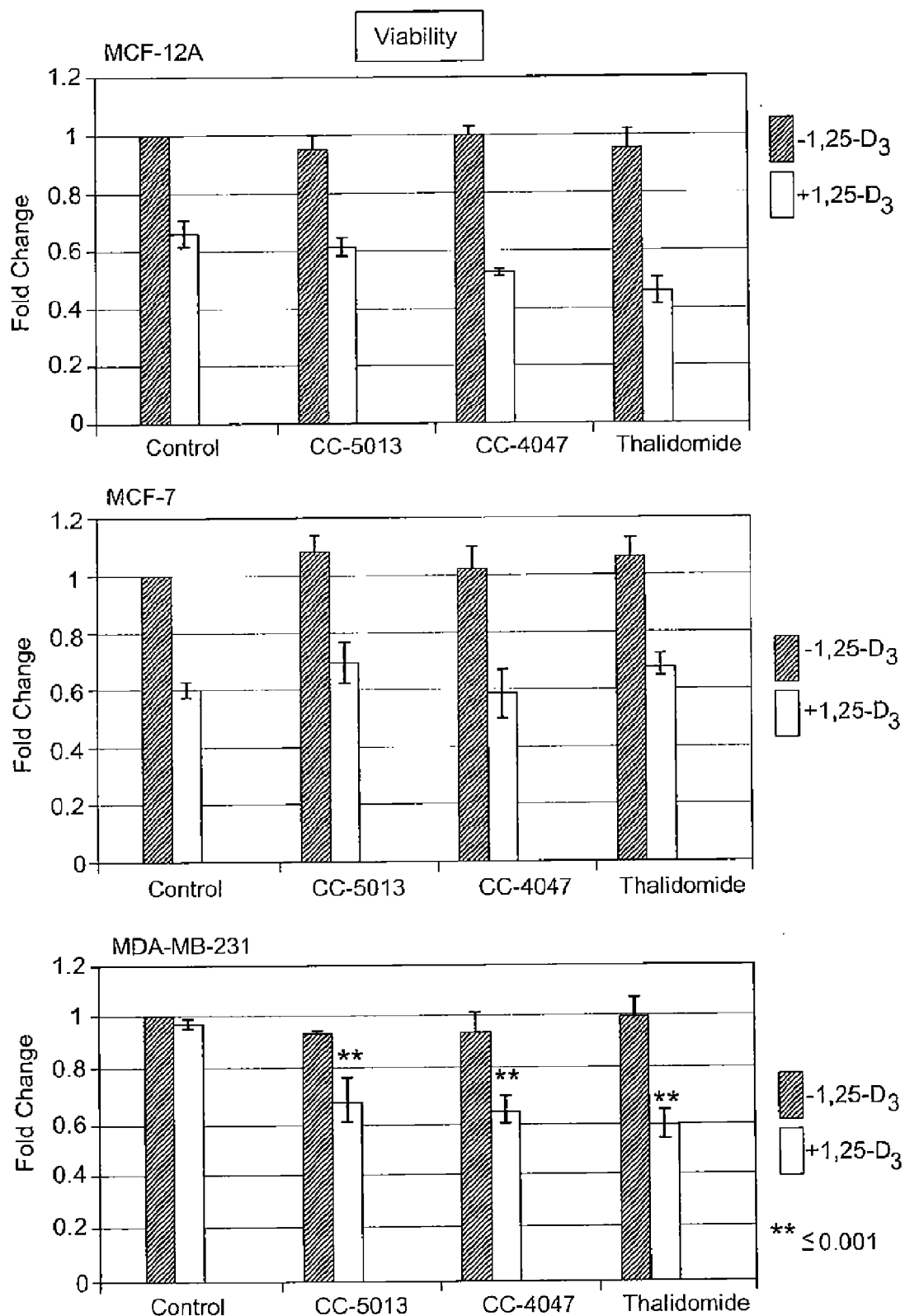
FIG. 7 illustrates the effects of co-treatment IMiDs/1, 25-$D_3$ on growth and viability of different breast cancer cell lines.
Figure 7B:
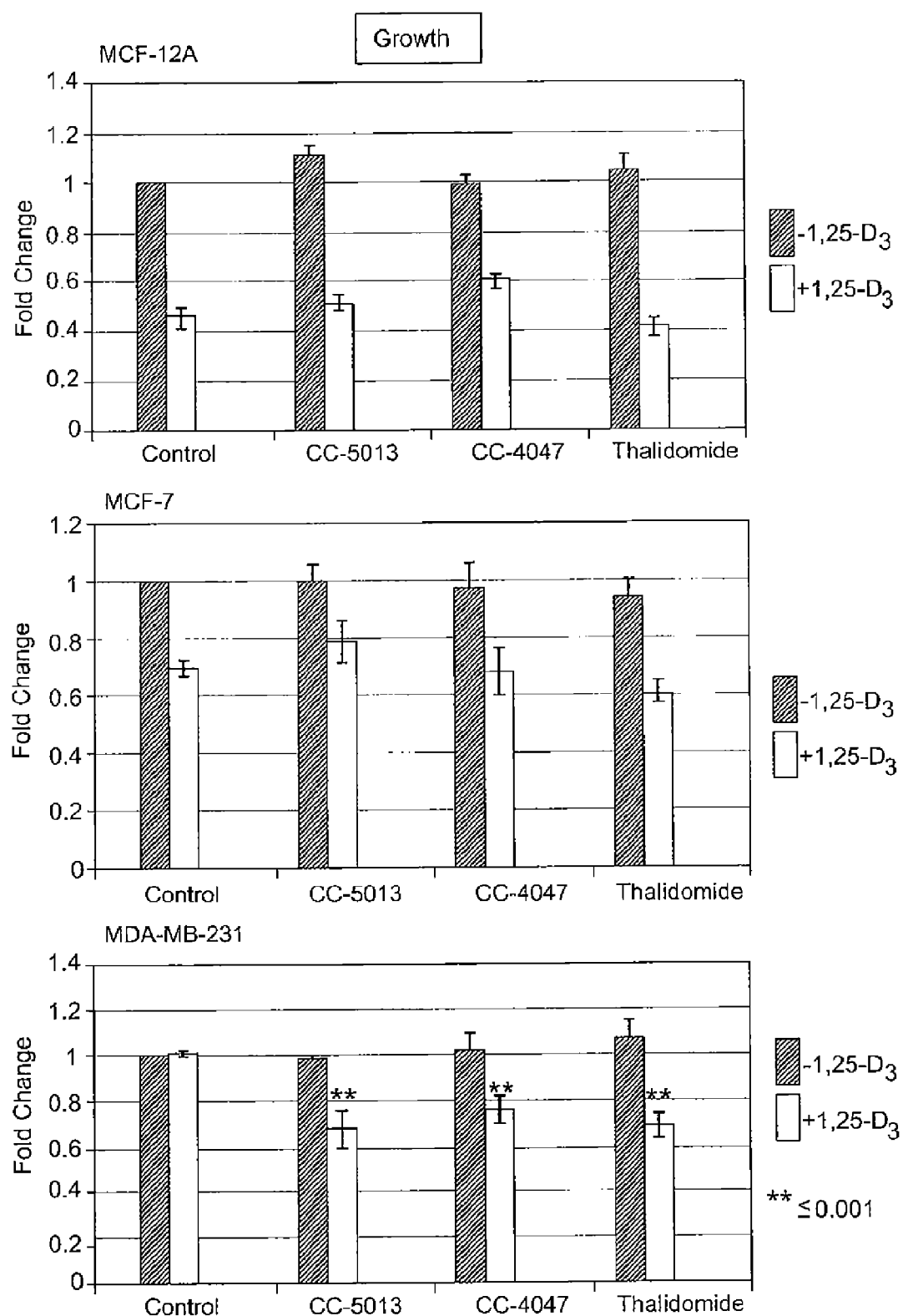

MCF-12A, MCF-7 and MDA-MB-231 cells were treated for up to 6 days with 1 µM of different IMiDs and 100 nM 1,25-$D_3$, alone or in combination. The effects of this treatment are shown in FIG. 7. Cells were also treated with 0.1% DMSO as a control. (7A) illustrates cell viability was measured by neutral red dye assay. (7B) illustrates cell growth was estimated by SRB assay. **($p<0.001$ by 1 way anova and Newman Keuls post test) Statistics have been performed comparing the significance between control (DMSO as a vehicle) and treated cells.

As described above, IMiD treatments have no effect on MCF-7 and MCF-12A cell viability and growth. 1,25-$D_3$ treatment inhibits MCF-12A and MCF-7 viability by 35% and 40% respectively and also growth by 55% for MCF-12A cells and 30% for MCF-7 cells. However, the addition of IMiDs in co-treatment with 1,25-$D_3$ does not change the effects of 1,25-$D_3$ on cell growth and viability. 1,25-$D_3$ and IMiDs treatments alone have no effect on MDA-MB-231 cell growth and viability. However, MDA-MB-231 co-treated with 1,25-$D_3$ and the IMiD lenalidomide leads to inhibition of cell viability (30 to 35% of inhibition ($p<0.001$)) and cell growth (22 to 35% inhibition ($p<0.001$)). These results suggest a synergistic effect of 1,25-$D_3$ and lenalidomide on the inhibition of MDA-MB-231 cell growth and activation of cell death. We decided to focus our study on the effects of co-treatment lenalidomide/1, 25-$D_3$ on MDA-MB-231 cells to understand the mechanism of this synergistic effect leading to MDA-MB-231 cell death.

Figure 12:
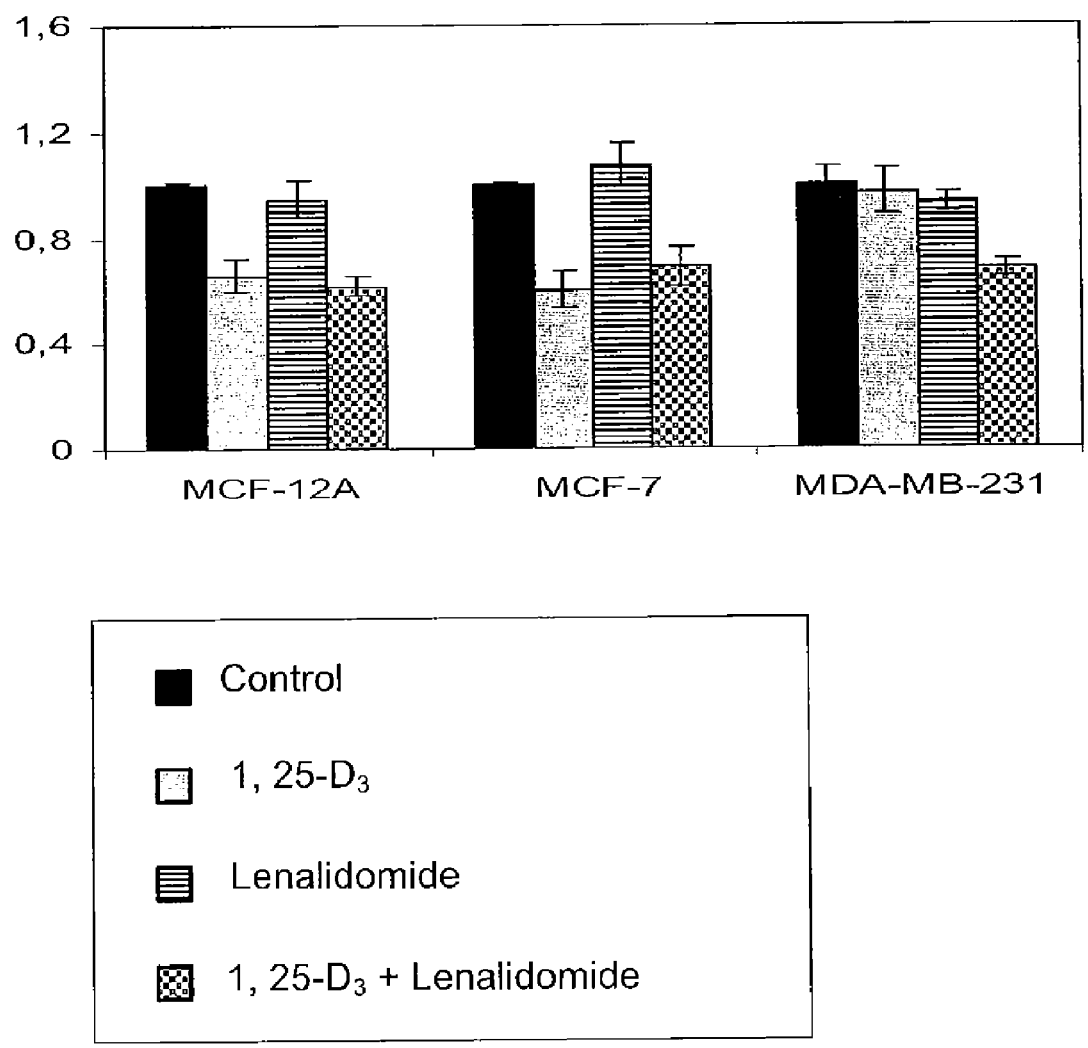
FIG. 12 illustrates the effects of 1, 25-D3 and lenalidomide treatment, alone or in combination, on breast cancer cell line viability.

FIG. 12 illustrates the effects of 1, 25-D3 and lenalidomide treatment, alone or in combination, on breast cancer cell line viability.

Determination of the Nature of MDA-MB-231 Death Induced by Lenalidomide/1, 25-$D_3$ Co-Treatment.

Figure 8:
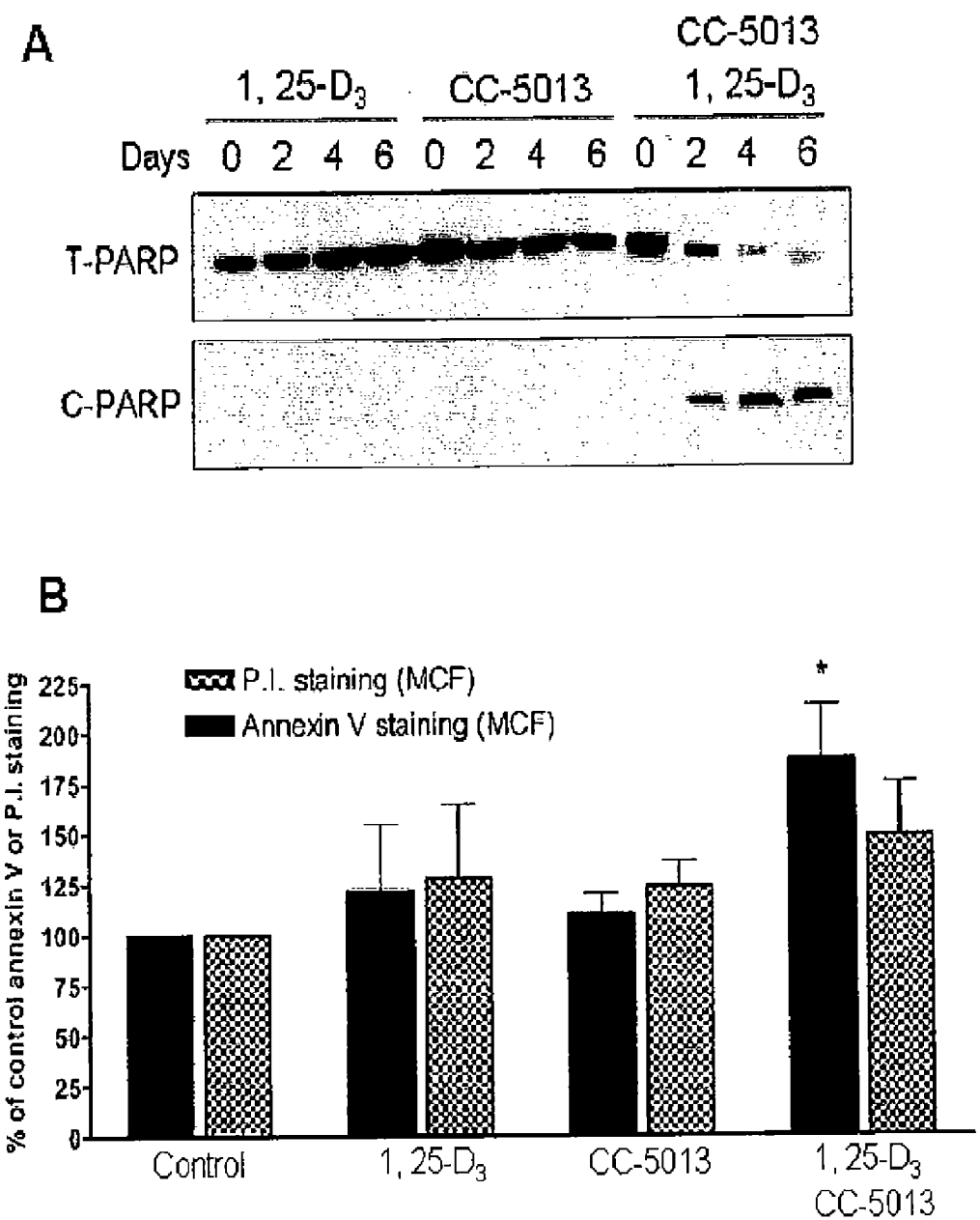
FIG. 8 illustrates the determination of the nature of MDA-MB-231 death induced by co-treatment lenalidomide/1, 25-$D_3$.

FIG. 8 illustrates this treatment where MDA-MB-231 cells were treated for up to 6 days with 1 µM lenalidomide and 100 nM 1,25-$D_3$ alone or in combination. Cells were also treated with 0.1% DMSO as a control. (8A) shows whole proteins were extracted from the cells after 2, 4 and 6 days of treatment. Cells treated with 0.1% DMSO were used as a control (day 0). Cell lysates were probed for cleaved-PARP(C-PARP) and total PARP (T-PARP). Data shown are representative of three identical experiments. (8B) shows cells were staining for Propidium iodide and Annexin V and analysed by FACS. *($p<0.005$ compared to untreated control by 1 way anova and Newman Keuls post test) Statistics have been performed comparing the significance between control (DMSO as a vehicle) and treated cells.

In order to determine the nature of cell death induced by co-treatment lenalidomide and 1,25-$D_3$ treatment on MDA-MB-231 cells, poly(ADP-ribose) polymerase 1 (PARP) cleavage was investigated by Western blot (8A). Indeed, PARP which is normally involved in DNA repair, DNA stability, and other cellular events, is cleaved by members of the caspase family during early apoptosis. Cleaved PARP is one of the most used diagnostic tools for the detection of apoptosis in many cell types (Koh et al., 2005). Whole proteins were extracted from the cells after 2, 4 and 6 days of treatment. Cells treated with 0.1% DMSO were used as a control (day 0). Lenalidomide and 1,25-$D_3$ treatment alone has no effect on PARP cleavage in MDA-MB-231. However, when both drugs are combined, PARP starts to be cleaved after 2 days of treatment. We can conclude that MDA-MB-231 death induced by co-treatment lenalidomide/1, 25-$D_3$ is mediated by apoptosis. In order to confirm this result, a FACS analysis was performed staining propidium iodide and Annexin V expression in the treated cells (these are markers of necrosis and apoptosis respectively) (8B). Lenalidomide and 1,25-$D_3$ treatment has no effects on necrosis and apoptosis activation. However, Annexin V staining was observed with co-treatment lenalidomide/1, 25-$D_3$. We confirmed here that the MDA-MB-231 cell death induced by co-treatment lenalidomide/1, 25-$D_3$ is mediated by apoptosis.

Determination of Proteins Involved in the Increased Apoptosis Seen with The Lenalidomide/1, 25-$D_3$ Co-Treatment with on Activation of Protein Leading to MDA-MB-231 Apoptosis.

Figure 9:
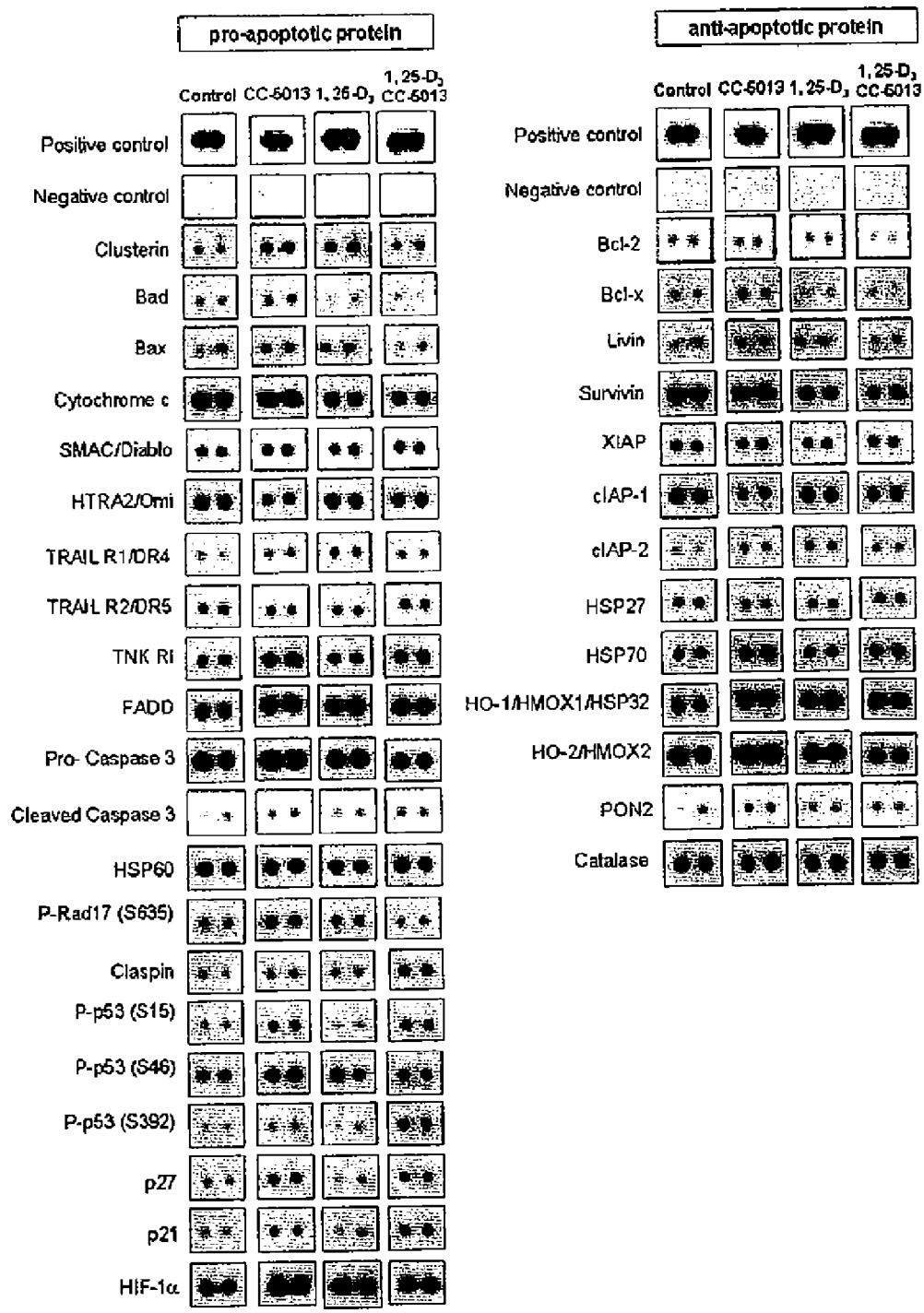
FIG. 9 illustrates the effects of co-treatment of lenalidomide/1, 25-$D_3$ on activation of protein leading to MDA-MB-231 apoptosis.

To determine the pathways and proteins involved in the increased apoptosis seen with the lenalidomide/1, 25-$D_3$ combination treatment, whole proteins were extracted from cells taken from the different treatments and were used for probing with an apoptosis protein array, according to the manufacturer. FIG. 9 illustrates the effects. MDA-MB-231 cells were treated for up to 6 days with 1 µM lenalidomide and 100 nM 1,25-$D_3$ alone or in combination. Cells were also treated with 0.1% DMSO as a control. Cells were lysed with RIPA buffer as described in the materials and methods, and 300 µg of protein from each of the samples was used for probing with the R& D apoptosis array according to the manufacturers instructions. Results are representative of 2 separate arrays performed. The protein array gives a semi quantitative analysis of changes in the key apoptosis and checkpoint pathway proteins. Co-treatment with lenalidomide/1, 25-$D_3$ (and lenalidomide only) induces p53 activation and phosphorylation of serine 15 and serine 392 was detected. It also induces activation of p21, p27 and claspin expression. All these proteins are well known to be major pro-apoptotic or checkpoint regulatory proteins. Lenalidomide or 1, 25-$D_3$ treatment alone does not affect the expression of the anti-apoptotic protein Bcl-2, which can explain the survival of MDA-MB-231 cells after these treatments, however co-treatment with lenalidomide/1, 25-$D_3$ inhibits BCL-2 expression. All theses results were confirmed by Western blot (FIG. 10 (a)) and densitometry plots of the array and western blot bands/dots were carried out to quantitate the changed expression of these proteins (FIG. 10 (b)). Therefore, the increase in pro-apoptotic proteins coupled with a decrease in Bcl-2 may be responsible for the increased apoptosis seen with the combination treatment.

Figure 10A:
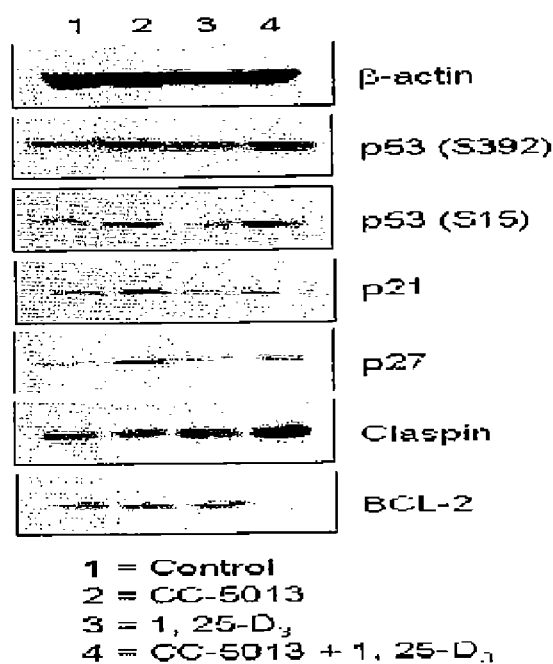
FIG. 10 illustrates the effects of co-treatment of lenalidomide/1, 25-$D_3$ on p53 activation and p21, p27, claspin, and BCL-2 protein expression in MDA-MB-231 cells.
Figure 10B:
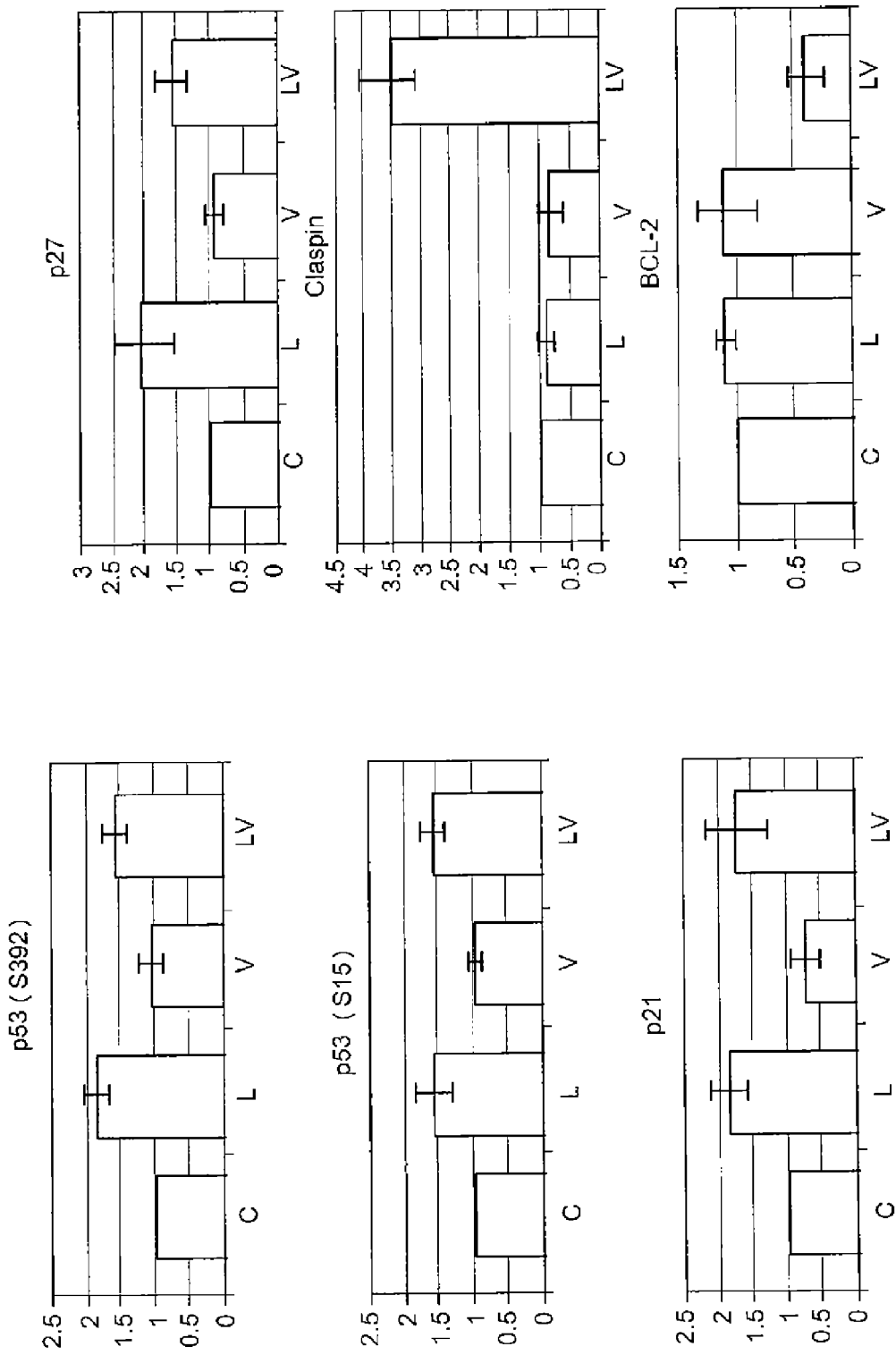

More particularly, FIG. 10 illustrates the effects of co-treatment lenalidomide/1, 25-$D_3$ on p53 activation and p21, p27, claspin, and BCL-2 protein expression in MDA-MB-231 cells. MDA-MB-231 cells were treated for up to 6 days with 1 µM lenalidomide and 100 nM 1,25-$D_3$ alone or in combination. Cells were also treated with 0.1% DMSO as a control. Whole proteins were extracted and probed for p53 (serine 15 and serine 392), p21, p27, claspin, and BCL-2, with b-actin as a house-keeping protein. Representative blots for the three experiments are shown (FIG. 10 (a)), and density index plots of the proteins (where the control has an index value of 1) are displayed in FIG. 10 (b) (n=5 from bands/dots taken from the array and western blot).

Lenalidomide/1, 25-$D_3$ Co-Treatment has No Effect on AKT and ERK1/2 Activation and VDR Protein Expression in MDA-MB-231 Cells.

Figure 11:
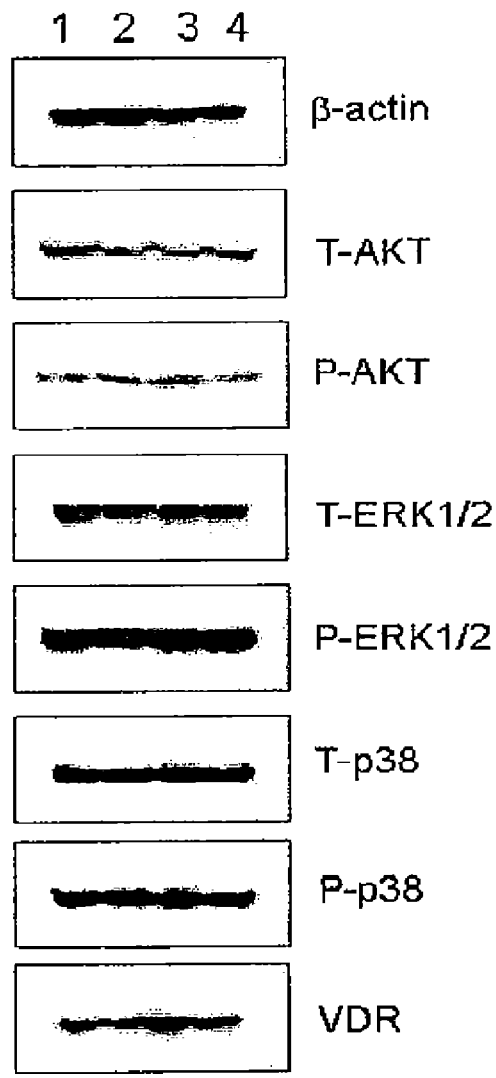
FIG. 11 illustrates the effects of co-treatment of lenalidomide/1, 25-$D_3$ co-treatment on expression of key signalling proteins in MDA-MB-231 cells.

To determine whether lenalidomide/1, 25-$D_3$ co-treatment had an effect on key growth signalling proteins, treated cells were lysed as shown in the materials and methods and Whole proteins were extracted and probed for total AKT (T-AKT), phosphor-AKT (P-AKT), total ERK1/2 (T-ERK1/2), phospho-ERK1/2 (P-ERK1/2), VDR and b-actin as a house-keeping protein. FIG. 11 shows a representative blots from the three experiments. No effects on the expression of these proteins is seen in any of the treatments.

More particularly, FIG. 11 illustrates the effects of co-treatment lenalidomide/1, 25-$D_3$ on expression of key signalling proteins in MDA-MB-231 cells. MDA-MB-231 cells were treated for 6 days with 1 µM lenalidomide and 100 nM 1,25-$D_3$ alone or in combination. Cells were also treated with 0.1% DMSO as a control. Whole proteins were extracted and probed for total AKT (T-AKT), phosphor-AKT (P-AKT), total ERK1/2 (T-ERK1/2), phospho-ERK1/2 (P-ERK1/2), phosphor-p38 and total p38, VDR and b-actin as a house-keeping protein. Representative blots for the three experiments are shown.

Effects of Lenalidomide and 1,25-$D_3$ Treatment on MCF-7/$VD^R$ and HBL-100 Viability In order to validate the previous results obtained in MDA-MB-231 cells, two other vitamin D resistant cell lines MCF-7/$VD^R$ and HBL-100 cells, were investigated. First the effect of lenalidomide on these cells lines were investigated. To this end, cells were treated for up to 6 days with different concentrations of lenalidomide (0 µM up to 10 µM). Cell viability was measured by neutal red dye assay (FIG. 13). No significant differences in viability of MCF-7/$VD^R$ and HBL-100 cells were detected after lenalidomide treatment (p>0.05).

More particularly, FIG. 13 illustrates the effects of lenalidomide treatment on MCF-7/VDR and HBL-100 viability. MCF-7/VDR and HBL-100 cells were treated for up to 6 days with different concentrations of lenalidomide (0 µM up to 10 µM). Cell viability was measured by neutral red dye assay. Results are mean of three independent experiments (each made in quadruplicate).

Figure 14:
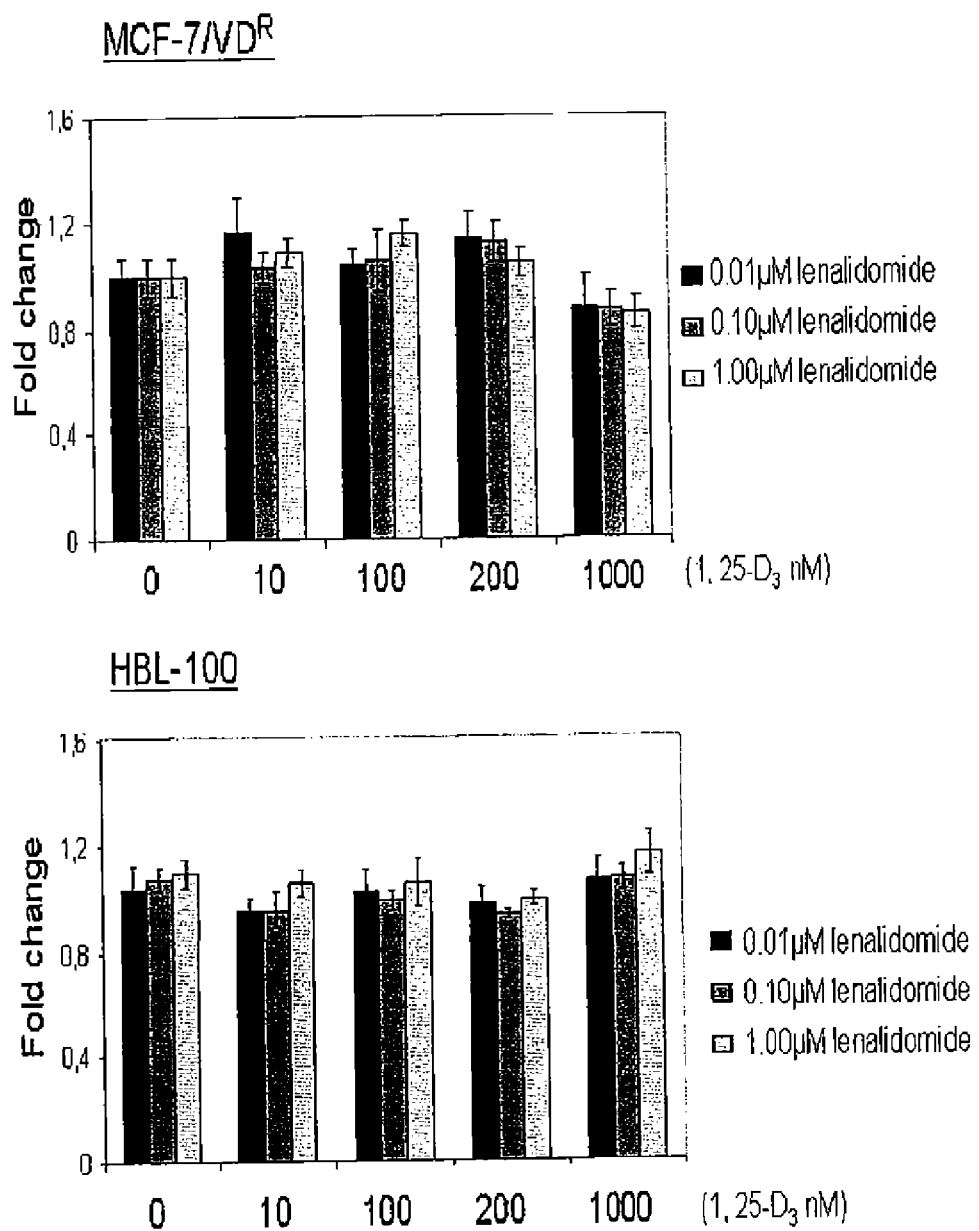
FIG. 14 illustrates the effects of lenalidomide/1, 25-$D_3$ co-treatment on MCF-7/VD$^R$ and HBL-100 viability.

Then, as previously performed in MDA-MB-231 cells, MCF-7/$VD^R$ and HBL-100 cells were treated for up to 6 days with different concentrations of lenalidomide (0.01 µM up to 1 µM) alone or in combination with different concentrations of 1,25-$D_3$ (0 up to 1000 nM). Cell viability was measured by neutral red dye assay (FIG. 14). No significant differences in viability of MCF-7/$VD^R$ and HBL-100 cells were detected with these treatments, alone or in combination (p>0.05).

More particularly, FIG. 14 illustrates the effects of lenalidomide/1, 25-D3 co-treatment on MCF-7/VDR and HBL-100 viability. MCF-7/VDR and HBL-100 cells were treated for up to 6 days with different concentrations of lenalidomide (0.01 µM up to 1 µM) alone or in combination with different concentrations of 1, 25-D3 (0 for up to 1000 nM). Cell viability was measured by neutral red dye assay. Results are mean of three independent experiments (each made in quadruplicate).

Like MDA-MB-231 cells, MCF-7/$VD^R$ and HBL-100 cells are resistant to lenalidomide and 1,25-$D_3$ treatment. However in these cell lines, combination treatment failed to restore a vitamin D sensitive phenotype to these vitamin D resistant breast cancer cell lines.

Effects of Lenalidomide/1, 25-$D_3$ Co-Treament on BCL-2 Expression in MCF-7/$VD^R$ and HBL-100 Cells.

It has been shown in this paper that BCL-2 inhibition of expression seems to be a key event for the restoration of a sensitive vitamin D sensitive phenotype in MDA-MB-231. Because co-treatment with lenalidomide/1, 25-$D_3$ failed to restore a vitamin D sensitive phenotype to MCF-7/$VD^R$ and HBL-100 cells, effects of these treatments on BCL-2 expression were investigated. Therefore, cells were treated for 6 days with 1 µM lenalidomide and 100 nM 1,25-$D_3$ alone or in combination. Cells were also treated with 0.1% DMSO as a control. Whole cells extracts were prepared and analysed by immuoblotting BCL-2 antibody. β-actin was used as a loading control. In both cell lines, lenalidomide and 1, 23-$D_3$ treatments, alone or in combination, had no effects on BCL-2 expression (FIG. 15).

Figure 15:
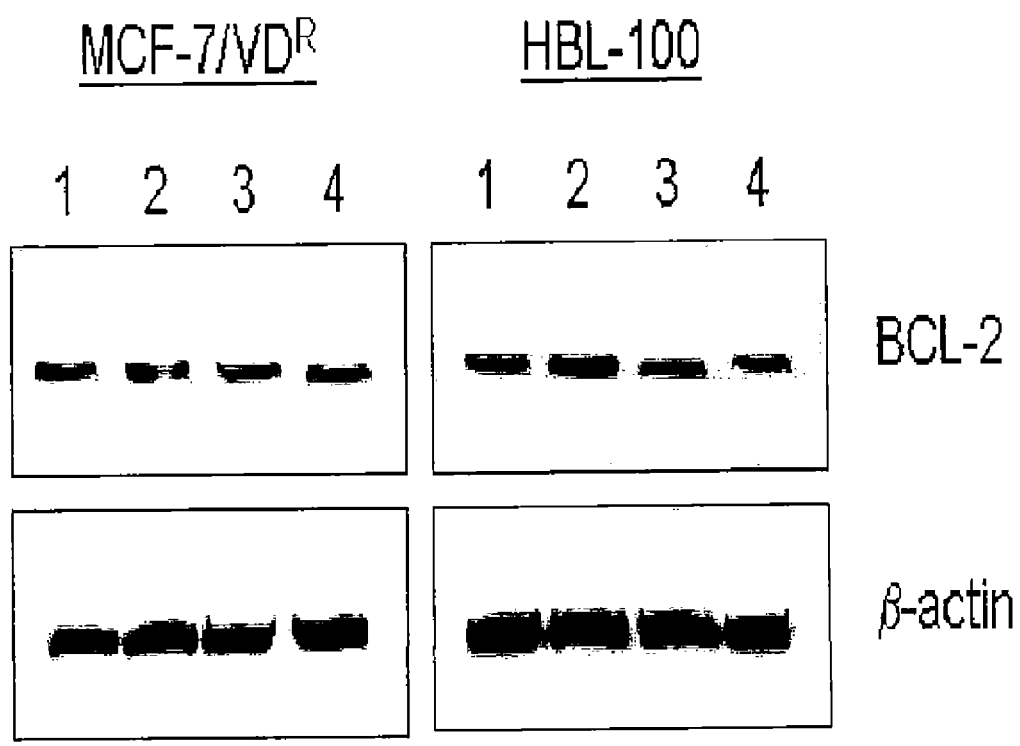
FIG. 15 illustrates the effects of co-treatment lenalidomide/1, 25-$D_3$ on BCL-2 expression in MCF-7VD$^R$ and HBL-100 cells.

More particularly, FIG. 15 illustrates the effects of co-treatment lenalidomide/1, 25-D3 on BCL-2 expression in MCF-7VDR and HBL-100 cells. MCF-7/VDR and HBL-100 cells were treated for up to 6 days with 1 µM lenalidomide and 100 nM 1, 25-D3 alone or in combination. Cells were also treated with 0.1% DMSO a control. Whole proteins were extracted and probes for BCL-2. β-actin was used as a loading control. Representative blots for the three experiments are shown.

Effects of BCL-2 Inhibition on MDA-MB-231, MCF-7ND$^R$ and HBL-100 Viability.

Figure 16:
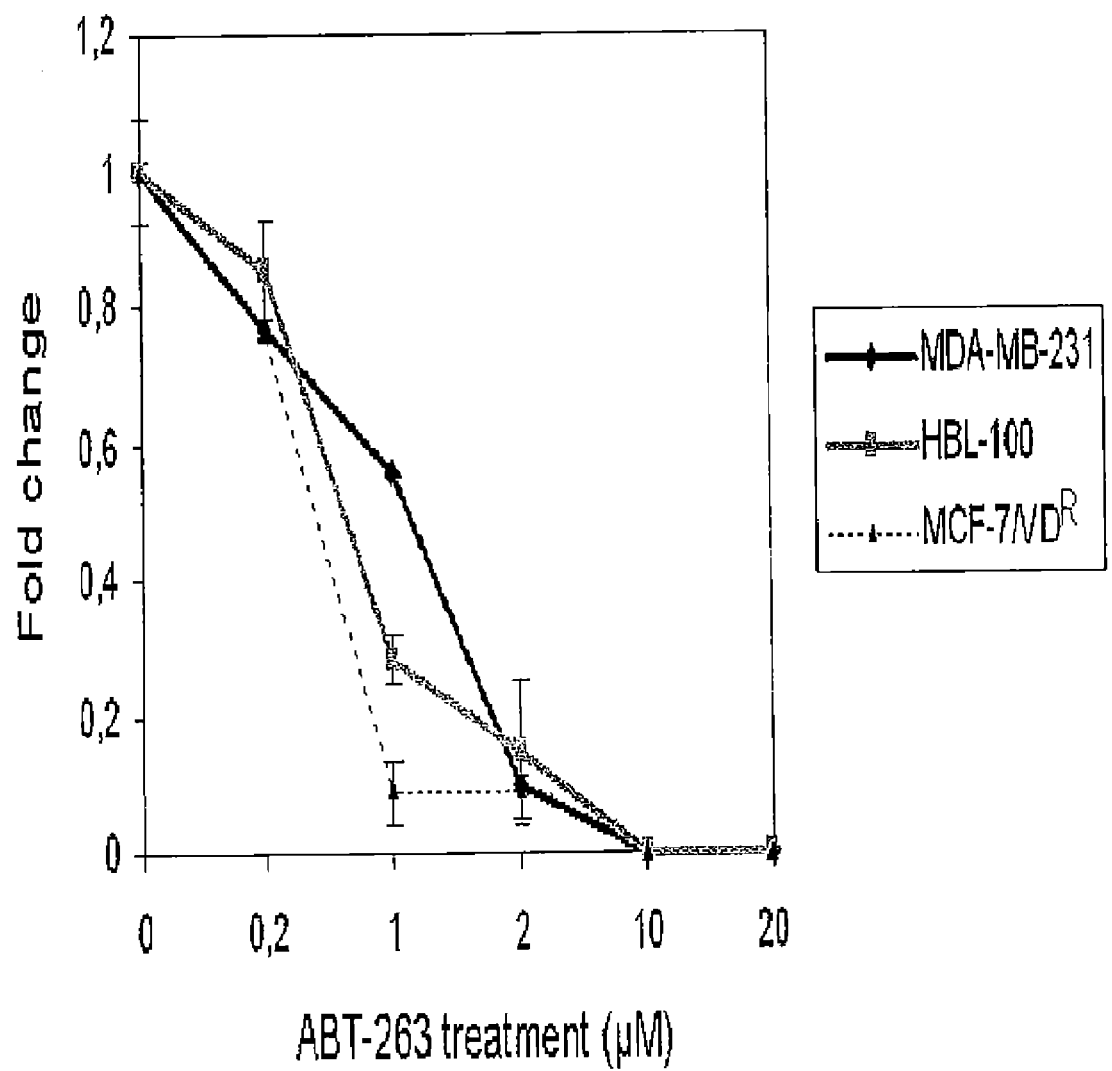
FIG. 16 illustrates the effects of BCL-2 inhibition on MCF-7VD$^R$ and HBL-100 viability.

This last experiment was performed in order to show that BCL-2 inhibition of expression is enough to induce cell death in MDA-MB-231, MCF-7/VD$^R$ and HBL-100 cells. To accomplish this, cells were treated for up to 6 days with different concentrations of a BCL-2 inhibitor, ABT-263 (0.2 μM). Non-treated cells were used as a control. After 6 days of treatment, cell viability was measured by neutral red assay (FIG. 16). In the three cell lines, BCL-2 inhibition leads to cell death. The IC$_{50}$ is almost equivalent in all cell lines (1 μM+/−0.2 μM).

More particularly, FIG. 16 illustrates the effects of BCL-2 inhibition on MCF-7VD$^R$ and HBL-100 viability. MDA-MB-231, MCF-7/VD$^R$ and HBL-100 cells were treated for up to 6 days with different concentrations of ABT-263 (0.2 up to 20 μM). Non-treated cells were used as a control. After 6 days of treatment, cell viability was measured by neutral red assay. Results are mean of three independent experiments (each made in quadruplicate).

Discussion

In this study, we demonstrate that lenalidomide restores the sensitivity to vitamin D of a cell line that is completely refractory to its effects. In sensitive cells, 1, 25 D3 acts on the Vitamin D receptor to trigger a signalling cascade leading to apoptosis and growth arrest. FIG. 6 shows the growth and apoptotic pathways involved in the actions of vitamin D in breast cancer cells. In MCF-7 cells, 1, 25 D3 acts through the p21 cascade to induce growth arrest, BCL-2 is downregulated to promote apoptosis (Mathiasen, I. S. et al. Cancer Res. 59, 4848-4856 (1999)).

We first examined the direct effects of the IMiDs, thalidomide, pomalidomide and lenalidomide as single agents on three breast cancer cell lines, MCF12A, MCF-7 and MBA-MD-231. There was no effect on the growth or viability of MCF12A or MCF-7, and only minor effects on the growth of the MBA-MD-231 at the highest doses of the IMiDs. The IMiDs therefore are not anti-proliferative or cytotoxic agents when administered on their own. When the IMiDs were combined with 1,25 D3, there was no additive effect of the drugs on the existing action of the agent in MCF12A and MCF-7 cells, however, in the vitamin D resistant cell line, MBA-MD-231, vitamin D sensitivity was restored by physiological doses of the IMiDs, and 100 nM of 1,25 D3 gave the same inhibition of growth and toxicity in MBA-MD-231 and MCF-7 cells. We selected the lead therapeutically used IMiD, lenalidomide, for analysis of the molecular mechanisms of this effect.

We initially studied the ability of 1,25 D3 and lenalidomide, as single agents or in combination, to affect apoptosis in the MBA-MD-231 cell line, as this is a key mechanism by which 1,25 D3 mediates its anti-tumour effects in MCF-7 and breast cancer cells. We observed that apoptosis, as measured by annexin V staining, and PARP cleavage, was significantly increased in MBA-MD-231 cells treated with lenalidomide and vitamin D compared to cells treated with the single agents or the DMSO control.

To determine the proteins of the apoptotic pathway that were significantly changed with lenalidomide and vitamin D treatment compared to other treatments, we used protein array and confirmatory blot analyses in the MBA-MD-231 cell line. The protein array analysis was used initially to screen a number of proteins in the apoptotic and growth arrest pathways with a semi-quantitative analysis. From the array, we showed that the proapoptotic proteins P21, P27 and P53S392 are upregulated upon treatment with lenalidomide on its own and in combination with vitamin D.

The proapoptotic protein claspin is upregulated by the combination, but not with either agent alone, and the expression of the anti-apoptotic protein BCL2 is abolished by the combination. These changes were confirmed with western blotting assays using these proteins. Combining 1,25D$_3$ and lenalidomide therefore caused an altered expression of anti-proapoptotic and pro-apoptotic proteins leading to an overall increase in apoptosis, compared to treatment with 1, 25D$_3$ alone. The moist striking result was the abolition of BC1-2 expression in the MDA-MB-231 cell line resulting in increased capase activity and greatly increased PARP cleavage. The combination caused no changes in the expression of VDR or key growth signaling proteins such as pAKT, pERK or pJNK.

The anti-apoptotic protein BCL-2 is a common therapeutic target for inhibition of growth of solid tumours and phase I/II clinical trials have now begun with BCL-2 inhibitors (Manion, M. K. et al. Curr. Opin. Investig. Drugs 7, 1077-1084 (2006) and Manion, M. K. et al. Cancer Biol. Ther. 2, S105-S114 (2003)). We considered that the inhibition of BC1-2 in the presence of both 1, 25D$_3$ and lenalidomide was the mechanism for the increasing cell killing in the MBA-MD-231 cell line. We therefore determined whether a specific inhibitor of BCL-2, ABT263 (Tse, C. et al. Cancer Res. 68, 3421-3428 (2008) and Shoemaker, A. R. et al. Clin Cancer Res. 14, 3268-3277 (2008) and Ackler, S. et al. Cancer Chemother. Pharmacol. (2010)), would be able to cause cell death in the MBA-MD-231 cell line, and other cell lines that were resistant to vitamin D. The inhibitor did indeed induce killing of the MBA-MD-231 cell and the other two vitamin D resistant lines HBL 100 and MCF-7 vitD res. The IC50s for killing of these cell lines were similar with ABT263 (1 μM). However, when we examined the effect of the lenalidomide/1,25D$_3$ combination on the HBL100 and the MCF7VitD res cell line, there was no inhibition of killing with lenalidomide, 1,25D$_3$ or the two drugs combined, and different titrations of the two drugs also did not result in killing of these two cell lines. We therefore examined the effects of the combination treatment on the expression of BCL-2 in these cell lines. The combination of 1,25D$_3$ and lenalidomide which caused an inhibition of BCL-2 in the MDA-MB-231 cell line was not however enough to inhibit the expression of BCL-2 in the HBL100 and MCF7 vitDR cell lines. This may be due to the higher expression of BCL-2 in these two cell lines compared with that seen in the MDA-MB-231 cell line. It is therefore possible that in cell lines that are not killed by 1,25D$_3$ and lenalidomide combination alone, the 1,25D$_3$/lenalidomide combination may be used in combination with lower concentrations of BC1-2 inhibitors to inhibit killing. This would be a more suitable strategy than using BCL-2 inhibitors alone, as resistance to these drugs develops relatively quickly. (Vogler, M. et al. Blood 113, 4403-4413 (2009) and Volger, M, et al. Cell Death. Differ. 16, 360-367 (2009).

Our results demonstrate: the immunomodulatory drug lenalidomide restores the vitamin D sensitive phenotype to resistant MDA-MB-231 breast cancer cells; apoptotic cell death of MDA-MB-231 cells is induced by co-treatment with 1, 25-D3/Lenalidomide; the combination of 1, 25 D3 and lenalidomide results in an increase in pro-apoptotic proteins (phosphorylated p53, p21, p27 and claspin), and a decrease in the anti-apoptotic protein bcl-2; and the combination of 1, 25 D3 and lenalidomide had no effect on p38, AKT and ERK.

These results demonstrate a potential use for lenalidomide in combination with 1, 25 D3 to target tumours that are refractory to vitamin D.

In summary, 1α,25-Dihydroxyvitamin D3, (1,25 D3) the biologically active form of vitamin D, is well established as an inhibitor of cancer cell growth in addition to its primary role in maintaining bone mineralization. In breast cancer cell lines, inhibitory effects on cell cycle arrest, angiogenesis, invasion and metastasis have been observed in addition to pro-apoptotic effects. (1,25 D3) also inhibits and prevents breast cancer growth in several mouse models, and a correlation between vitamin D receptor expression on breast cancer cells and disease free survival of breast cancer patients has also been observed. However, resistance to vitamin D and hypercalcaemia at higher doses are key limiting factors in clinical use. The drug revlimid (lenalidomide) which has shown great promise in multiple myeloma can also modulate signalling in apoptotic and cell growth pathways leading to inhibition of cell growth, inhibition of metastasis and invasion. Our study aimed to determine whether lenalidomide treatment of breast cancer cells resistant to vitamin D would result in an acquisition of sensitivity to vitamin D and a resultant inhibition of cell growth. The cell lines MCF-12A, MCF-7 and MDA-MB-231, representing non-tumorogenic, tumourogenic and metastatic breast lines respectively were used. The latter line was also vitamin D resistant. Cells were treated with lenalidomide and/or 1,25 D3 using a dose of 100 nM 1,25 D3 (a clinically tolerable dose giving IC50 inhibition of MCF-7 and MCF-12A cells). Results showed that whereas lenalidomide had no effect on the growth of the vitamin D sensitive lines, and gave only 20% inhibition of growth of MDA-MB-231 at 10 µM, a 50% inhibition of cell growth by 1,25 D3 (equivalent to that seen with the sensitive lines) was achieved in the presence of lenalidomide at a concentration of 1 µM. Further investigation revealed that the mechanism of this effect was an increase in apoptosis of the cell line, shown by an increase in parp cleavage and annexin V expression. An array measuring proteins associated with several signalling cascades showed that the combination of 1,25 D3 and lenalidomide resulted in an increase in proapoptotic proteins (phosphorylated P53, P21 and claspin, in addition to a decrease in BCL-2). Although both drugs had individual effects on pro-apotic proteins, and anti-apoptotic proteins, the combination resulted in an overall increase of pro-apoptotic protein expression leading to the observed inhibition of cell viability and growth. These results demonstrate the potential for the use of lenalidomide and 1, 25 D3 in combination for tumours that are refractory to vitamin D.

These examples also demonstrate the ability of lenalidomide to restore sensitivity of a vitamin D resistant cell line MDA-MB-231, to vitamin D, resulting in apoptosis of the cell line corresponding with a inhibition of BCL-2. We propose that BC1-2 is the molecule targeted by the two drugs in this cell line, as the combination does not cause killing of other vitamin D resistant cell lines where BCL-2 is not affected. The detailed mechanism by which the 1,25D$_3$/lenalidomide combination affects BCL-2 expression in this line still needs additional experimentation, however, the shift in the balance of expression of apoptotic and pro-survival proteins may be a key contributory factor and demonstrates a therapeutic strategy that could be exploited in breast cancers and other cancers with a high pro survival/apoptotic protein ratio.

The embodiments described above are intended to be merely exemplary, and those skilled in the art will recognize, or will be able to ascertain using no more than routine experimentation, numerous equivalents of specific compounds, materials, and procedures. All such equivalents are considered to be within the scope of the subject matter claimed and are encompassed by the appended claims.

What is claimed is:

1. A method of treating, managing or breast cancer refractory to vitamin D treatment, which comprises administering to a patient having such cancer an amount of an immunomodulatory compound, or a pharmaceutically acceptable salt, or stereoisomer thereof, in combination with a vitamin D agent, wherein the immunomodulatory compound is 4-(amino)-2-(2,6-dioxo-(3-piperidyl))-isoindoline-1,3-dione, or a pharmaceutically acceptable salt, or stereoisomer thereof, or 3-(4-amino-1-oxo-1,3-dihydro-isoindol-2-yl)-piperidine-2,6-dione, or a pharmaceutically acceptable salt, or stereoisomer thereof.

2. The method of claim 1, which further comprises administration of an additional active agent.

3. The method of claim 2, wherein the additional active agent is an anti-cancer agent.

4. The method of claim 1, wherein the vitamin D agent is 1α, 25-dihydroxyvitamin D$_3$.

5. The method of claim 1, wherein the immunomodulatory compound and the vitamin D agent are simultaneously administered.

6. The method of claim 1, wherein the immunomodulatory compound is administered prior to the administration of the vitamin D agent.

7. The method of claim 1, wherein the immunomodulatory compound and the vitamin D agent are administered using the same route.

8. The method of claim 7, wherein the immunomodulatory compound and the vitamin D agent are both orally administered.

9. The method of claim 1, wherein the immunomodulatory compound and the vitamin D agent are administered using different routes.

10. The method of claim 9, wherein the immunomodulatory compound is parenterally administered and the vitamin D agent is orally administered.

11. The method of claim 9, wherein the immunomodulatory compound is orally administered and the vitamin D agent is parenterally administered.

12. The method of claim 1, wherein the immunomodulatory compound is 3-(4-amino-1-oxo-1,3-dihydro-isoindol-2-yl)-piperidine-2,6-dione or a pharmaceutically acceptable salt, or stereoisomer thereof.

13. The method of claim 4, wherein the immunomodulatory compound is 3-(4-amino-1-oxo-1,3-dihydro-isoindol-2-yl)-piperidine-2,6-dione or a pharmaceutically acceptable salt, or stereoisomer thereof.

14. The method of claim 1, wherein the immunomodulatory compound is 4-(amino)-2-(2,6-dioxo-(3-piperidyl))-isoindoline-1,3-dione or a pharmaceutically acceptable salt, or stereoisomer thereof.

15. The method of claim 4, wherein the immunomodulatory compound is 4-(amino)-2-(2,6-dioxo-(3-piperidyl))-isoindoline-1,3-dione or a pharmaceutically acceptable salt, or stereoisomer thereof.

* * * * *